US008242238B2

(12) United States Patent
Krupka

(10) Patent No.: US 8,242,238 B2
(45) Date of Patent: Aug. 14, 2012

(54) SURFACE PROTEIN (HBSAG) VARIANT OF THE HEPATITIS B VIRUS

(75) Inventor: Udo Krupka, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 998 days.

(21) Appl. No.: 10/561,345

(22) PCT Filed: Jun. 17, 2004

(86) PCT No.: PCT/EP2004/006515
§ 371 (c)(1), (2), (4) Date: Dec. 20, 2005

(87) PCT Pub. No.: WO2004/113369
PCT Pub. Date: Dec. 29, 2004

(65) Prior Publication Data

US 2006/0194196 A1 Aug. 31, 2006

(30) Foreign Application Priority Data

Jun. 20, 2003 (DE) ................................ 103 28 080

(51) Int. Cl.
*C07K 5/00* (2006.01)
*C12Q 1/70* (2006.01)

(52) U.S. Cl. ................. 530/300; 424/204.1; 424/227.1; 435/5

(58) Field of Classification Search ........................ None
See application file for complete search history.

(56) References Cited

U.S. PATENT DOCUMENTS

| | | | | |
|---|---|---|---|---|
| 5,531,990 | A | 7/1996 | Thanavala et al. | |
| 5,856,084 | A * | 1/1999 | Karayiannis et al. | 435/5 |
| 7,485,312 | B2 | 2/2009 | Krupka | |

FOREIGN PATENT DOCUMENTS

| | | | |
|---|---|---|---|
| EP | 0 533 492 | * | 3/1993 |
| EP | 1 142 906 | A1 | 10/2001 |
| EP | 1 174 523 | A2 | 1/2002 |
| EP | 1 174 523 | A3 | 1/2002 |
| JP | 2002327000 | A | 11/2002 |
| WO | WO 93/05811 | A1 | 4/1993 |
| WO | WO 00/07631 | * | 2/2000 |
| WO | WO 01/40279 | A2 | 6/2001 |
| WO | WO 01/57244 | A1 | 8/2001 |
| WO | WO 02/079217 | | 10/2002 |
| WO | WO 2004/113370 | | 12/2004 |

OTHER PUBLICATIONS

S Preisler-Adams et al. "Complete nucleotide sequence of a hepatitis B virus, subtype adw2, and identification of three types of C open reading frame". Nucleic Acids Res. 21(9):2258, 1993.*

Abaza et al., "Effects of amino acid substitutions outside an antigenic site on protein binding to monoclonal antibodies of predetermined specificity obtained by peptide immunization: Demonstration with region 94-100 (antigenic site 3) of myoglobin ," Journal of Protein Chemistry, vol. 11 No. 5, pp. 433-444 (Oct. 1992).*

Bowie et al., "Deciphering the Message in Protein Sequences: Tolerance to Amino Acid Substitutions," Science, vol. 247 No. 4948, pp. 1306-1310 (Mar. 1990).*

Riffkin et al., "A single amino-acid change between the antigenically different extracellular serine proteases V2 and B2 from *Dichelobacter nodosus*," Gene, vol. 167 No. 1-2, pp. 279-283 (Dec. 1995).*

GenPept BAC17521, "putative amino-acid permease [Corynebacterium efficiens YS-314]," Oct. 2002.*

GenBank AAO41333, preS1/preS2 surface protein [Hepatitis B virus], Jun. 30, 2003.*

GenBank AAF36498, "S antigen [Hepatitis B virus].," Feb. 2000.*

R. Scopes, *Protein Purification: Principles and Practice* ($3^{rd}$ edition), Springer Verlag (1994), table of contents only.

E. Harlow et al., *Antibodies: A Laboratory Manual*, Cold Spring Harbor Laboratory Press (1988), table of contents only.

W. M. Lee, "Hepatitis B Virus Infection," *N. Engl. J. Med*, 337: 1733-1745 (1997).

P. Tiollais et al., "The hepatitis B virus," *Nature*, 317: 489-495 (1985).

W. H. Gerlich at al., "Functions of Hepatitis B Virus Proteins and Virus Assembly," *Viral Hepatitis and Liver Disease*, 121-134 (1991).

H. E. Blum, "Variants of Hepatitis B, C and D Viruses: Molecular Biology and Clinical Significance," *Digestion* 56: 85-95 (1995).

H. Okamoto et al., "Genomic Heterogeneity of Hepatitis B Virus in a 54-Year-Old Woman who Contracted the Infection through Materno-Fetal Transmission," *Jpn. J. Exp. Med.* 57: 231-236 (1987).

W. Carman et al., "Viral genetic variation: hepatitis B virus as a clinical example," *Lancet* 341:349-353 (1993).

A.M. Courouce Ed., Karger AG, Basel, Switzerland, *Bibliotheca Haematologica 42*: Table of Contents, pp. 1-19, (1976).

H. Norder et al., "Molecular basis of hepatitis B virus serotype variations within the four major subtypes," *J. Gen. Virol.* 73: 3141-3145 (1992).

H. Norder et al., "Complete Genomes, Phylogenetic Relatedness, and Structural Proteins of Six Strains of the Hepatitis B Virus, Four of Which Represent Two New Genotypes," *Virology* 198: 489-503 (1994).

N. A. Terrault et al., "Incidence and Clinical Consequences of Surface and Polymerase Gene Mutations in Liver Transplant Recipients on Hepatitis B Immunoglobulin," *Hepatology* 28:555-561 (1998).

H. L. Tillmann et al., "Mutational Pattern of Hepatitis B Virus on Sequential Therapy With Famciclovir and Lamivudine in Patients With Hepatitis B Virus Reinfection Occurring Under HBIg Immunoglobilin After Liver Transplantation," *Hepatology* 30: 244-256 (1999).

(Continued)

*Primary Examiner* — Agnieszka Boesen

(74) *Attorney, Agent, or Firm* — Finnegan, Henderson, Farabow, Garrett & Dunner, LLP.

(57) ABSTRACT

The invention relates to sequences of a novel variant of the Hepatitis B surface antigen (HBsAg) and to methods for detecting, in patient samples, nucleic acids, antigens and antibodies directed against the same.

23 Claims, 6 Drawing Sheets

OTHER PUBLICATIONS

C. M. Hunt et al., "Clinical Relevance of Hepatitis B Viral Mutations," *Hepatology* 31: 1037-1044 (2000).

M. P. Cooreman et al., "Vaccine- and Hepatitis B Immune Globulin-Induced Escape Mutations of Hepatitis B Virus Surface Antigen," *J. Biomed. Science* 8:237-247 (2001).

D. L. Peterson et al., "Antigenic Structure of Hepatitis B Surface Antigen: Identification of the "d" Subtype Determinant by Chemical Modification and Use of Monoclonal Antibodies," *J. Immunol.* 132:920-927 (1984).

W. Jilg, "Novel hepatitis B vaccines," *Vaccine* 16: S65-S68 (1998).

W. F. Carman et al., "Hepatitis B Virus Envelope Variation After Transplantation With and Without Hepatitis B Immune Globulin Prophylaxis," *Hepatology* 24:489-493 (1996).

R. Müller et al., "Liver transplantation in HBs antigen (HBsAg) carriers," *J. Hepatol.* 13:90-96 (1991).

D. Samuel et al., "Liver transplantation in European Patients with the Hepatitis B Surface Antigen," *N. Engl. J. Med.* 329:1842-1847 (1993).

A. Brind et al., "Evidence for selection of hepatitis B mutants after liver transplantation through peripheral blood mononuclear cell infection," *J. Hepatol.* 26:228-235 (1997).

L. Fischer et al., "Hepatitis B Virus Variants Associated With Clinically Severe Recurrence After Liver Transplantation," *Transplantation Proceedings* 31: 492-493 (1999).

M. G. Ghany et al., "Hepatitis B Virus S Mutants in Liver Transplant Recipients Who Were Reinfected Despite Hepatitis B Immune Globulin Prophylaxis,," *Hepatology* 27:213-222 (1998).

U. Protzer-Knolle et al., "Hepatitis B Virus With Antigenically Altered Hepatitis B Surface Antigen Is Selected by High-Dose Hepatitis B Immune Globulin After Liver Transplantation," *Hepatology* 27: 254-263 (1998).

W. F. Carman et al., "Genetic Variation in Hepatitis B Virus," *Gastroenterology* 102: 711-719 (1992).

W. F. Carman, "The clinical significance of surface antigen variants of hepatitis B Virus," *J. Viral Hepatol.* 4(suppl 1): 11-20 (1997).

P. D. Swenson et at., "Determination of HBsAg subtypes in different high risk populations using monoclonal antibodies," *J. Virol. Meth.* 33: 27-28 (1991).

L. Blitz et al., "Antigenic Diversity of hepatitis B Virus Strains of Genotype F in Amerindians and Other Population Groups from Venezuela," *J. Clin. Microbiol* 36: 648-651 (1998).

P. G. Ashton-Rick Ardt et al., "Mutations That Change the Immunological Subtype of Hepatitis B Virus Surface Antigen and Distinguish Between Antigenic and Immunogenic Determination," *J. Med. Virol.* 29: 204-214 (1989).

K. I. Ohba et al., "Relationships between serotypes and genotypes of hepatitis B virus: genetic classification of HBV by use of surface genes," *Virus. Res.* 39: 25-34 (1995).

W. F. Carman et al., "Fulminant reactivation of hepatitis B due to envelope protein mutant that escaped detection by monoclonal HBsAg ELISA," *Lancet* 345: 1406-1407 (1995).

H. Okamoto et al., "Mutations within the S Gene of Hepatitis B Virus Transmitted from Mothers to Babies Immunized with Hepatitis B Immune Globulin and Vaccine," *Pediatr. Res.* 32: 264.268 (1992).

Y. Y. Zhang et al., "Increasing Heterogeneity of the 'a' Determinant of HBsAg Found in the Presumed Late Phase of Chronic Hepatitis B Virus Infection," *J. Infect. Dis.* 28: 9-15 (1996).

A. J. Zuckermann at al., "Mutations in S region of hepatitis B virus," *Lancet* 343: 737-738 (1994).

T. F. Smith et al., "Comparison of Biosequences," *Adv. Appl Mathem.* 2: 482-489 (1981).

R. M. Schwartz et al., M. D. Dayhoff, Ed., "Matrices for Detecting Distant relationships," *Atlas of Protein Sequence and Structure Suppl 3*, pp. 353-358, Nat. Biomed. Res. Found., Washington D. C. (1978).

M. Gribskov et al., "Sigma factors from *E. coli, B. subtilis*, phage SP01, and phage T4 are homologous proteins," *Nucleic. Acids Research* 14: 6745-5763 (1986).

J. Sambrook et al., *Molecular Cloning*, vol. I, pp. xi-xxxviii, Cold Spring Harbor Lab. Press (1989).

M. Ausubel et al., *Current Protocols in Molecular Biology*, pp. iii-xviii, Greene Publishing (1992).

G. Köhler et al., "Continuous cultures of fused cells secreting antibody of predefined specificity," *Nature* 256: 495-497 (1975).

L. T. Mimms et al., "Discrimination of Hepatitis B Virus (HBV) Subtypes Using Monoclonal Antibodies to the PreS1 and PreS2 Domains of the Viral Envelope," *Virology* 176: 604-619 (1990).

EMBL GenBank DDBJ Database Entry Q8BAA5, submitted Jul. 2002, integrated Mar. 1, 2003.

S. J. Friezner Degen et al., "The Murine Urokinase-Type Plasminogen Activator Gene," *Biochemistry*, 26: 8270-8279 (1987).

K. M. Weinberger et al., "High genetic variability of the group-specific a-determinant of hepatitis B virus surface antigen (HBsAg) and the corresponding fragment of the viral polymerase in chronic virus carriers lacking detectable HBsAg in serum," *Journal of General Virology*, 81: 1165-1174 (2000).

M. P. Cooreman et al., "Characterization of the Reactivity Pattern of Murine Monoclonal Antibodies Against Wild-Type Hepatitis B Surface Antigen to G145R and Other Naturally Occuring "a" Loop Escape Mutations," *Hepatology*, 11: 1287-1292 (1999).

W. F. Carman et al., "Fulminant reactivation of hepatitis B due to envelope protein mutant that escaped detection by monoclonal HBsAg ELISA," *The Lancet*, 345: 1406-1407 (1995).

H-L. Chiou et al., "Altered antigenicity of 'a' determinant variants of hepatitis B virus," *Journal of General Virology*, 78: 2639-2645 (1997).

Sequence No. Q96841 from: M. T. Moraes et al., "Sequence analysis of pre-S/S gene of hepatitis B virus strains of genotypes A, D, and F isolates," *Arch. Virol.*, 141:1767-1773 (1996).

Sequence No. EMBL: AB104715 from: N. Saudy et al., " Genotypes and phylogenetic characterization of hepatitis B and delta viruses in Egypt," *Journal of Medical Virology*, 70(4): 529-536 (2003).

Sequence No. AF280817 from: L. Yan et al., "First Chinese HBV strain: genotype D complete sequence report," submitted (Jun. 21, 2000).

Sequence No. EMBL: HEB214660 from: I. Borchani-Chabchoub, "Genotyping of Tunisian hepatitis B virus isolates based on the sequencing of preS2 and S regions," *Microbes infect.*, 2(6): 607-612 (2000).

International Search Report for PCT/EP2004/006515 dated Oct. 15, 2004.

International Search Report for PCT/EP2004/006516 dated Sep. 21, 2004.

Restriction Requirement Dated Aug. 11, 2006 in U.S. Appl. No. 10/561,343.

Office Action dated Jan. 4, 2007 in U.S. Appl. No. 10/561,343.

Office Action dated Sep. 24, 2007 in U.S. Appl. No. 10/561,343.

Notice of Allowance dated Aug. 11, 2008 in U.S. Appl. 10/561,343.

Miscellaneous Communication to Applicant dated Dec. 8, 2008 in U.S. Appl. No. 10/561,343.

Quintero et al., Molecular epidemiology of hepatitis B virus in Afro-Venezuelan populations, *Arch. Virol.* (2002) 147:1829-1836; 2002.

Mbayed et al., Distribution of Hepatitis B virus genotypes in two different pediatric populations form Argentina, *Journal of Clinical Microbiology*, Nov. 1998; p. 3362-3365; 1998.

Cooreman et al.,"Characterization of the reactivity pattern of murine monoclonal antibodies against wild-type hepatitis B surface antigen to G145R and other naturally occurring "a" loop escape mutations", *Hepatology*, 1999, vol. 30, No. 5, p. 1287-1292; 1999.

\* cited by examiner

Fig. 1: Amino acid sequence of the HBsAg a determinant of the different HBV genotypes as compared with the novel mutant HDB 05

A representative genome was used as the basis for each genotype and the aa sequence was deduced from the nucleotide sequence A: X70 185; B: DO0331; C: XO1587; D: X72702, E: X75664; F: X75663; (Stuyver et al.; J. Gen. Virol. 81: 67-74 (2000); Norder et al.: J. Gen. Virol. 73: 3141-3145 (1992)

| aa # | 101 | 111 | 121 | 131 | 141 | 151 | 161 170 |
|---|---|---|---|---|---|---|---|
| Genotyp | | | | | | | |
| A | QGMLPVCPLI | PGSTTTSTGP | CKTCTI | PSCCCT | KPTDGNCTCI | PIPSSWAFAK | YLWEWASVRF |
| B | ---------- | ---S------ | ------ | ------ | ---------- | ---------- | ---------- |
| C | ---------L | --TS------ | -----I---- | T--------- | --S------- | ---------R | F---G------ |
| D | ---------- | ---S------ | -R-------- | T--Y------ | --S------- | --------G- | F------A-- |
| E | ---------- | ---S------ | -R--M-L--- | T--------S | --S------- | --------G- | F------A-- |
| F | ---------- | ---------- | ------L--- | T--------S | --S------- | -------LG- | -------A-- |
| HDB 05 | ---------- | ----R----Q | ---------- | ---------- | ---------- | ---L------ | ---V------ |
| aa # | | 115 120 | | | | 154 | 164 |

The amino acid substitutions which differ from the wild-type adw HBV are printed in bold type

Fig. 2 Nucleotide sequence of the S gene of the known HBV adw wild type encoding the HBV surface protein (surface antigen, HBsAg), and resulting amino acid sequence in the 3-letter and, especially, 1-letter codes (Coleman et al; WO 02/079217 A1) Continuous numbering of nucleotides (nt) encoding the surface antigen (excl. pre S1 and pre S2 regions) Continuous numbering of amino acids (aa)

Fig. 3  Nucleotide sequence of the HBV surface antigen-encoding S gene of the HBV adw wild type (upper row from nt 1 to nt 678) as compared with the nucleotide sequence, which is sequenced from nt 127 to nt 588, of the novel variant HDB 05 (lower row, in which nucleotide differences are printed in bold type and bracketed when the mutations do not lead to any amino acid substitution)

```
 1   ATG GAG AAC ATC ACA TCA GGA TTC CTA GGA CCC CTG CTC GTG TTA CAG GCG GGG TTT TTC        60

61   TTG TTG ACA AGA ATC CTC ACA ATA CCG CAG AGT CTA GAC TCG TGG TGG ACT TCT CTC AAT       120

121  TTT CTA GGG GGA TCA CCC GTG TGT CTT GGC CAA AAT TCG CAG TCC CCA ACC TCC AAT CAC
127:     GGG GGA TCA CCC GTG TGT CTT GGC CAA AAT TCG CAG TCC CCA ACC TCC AAT CAC       180

181  TCA CCA ACC TCC TGT CCT CCA ATT TGT CCT GGT TAT CGC TGG ATG TGT CTG CGG CGT TTT
     TCA CCA ACC TCC TGT CCT CCA ATT TGT CCT GGT TAT CGC TGG ATG TGT CTG CGG CGT TTT       240

241  ATC ATA TTC CTC TTC ATC CTG CTA TGC CTC ATC TTC TTA TTG GTT CTT CTG GAT TAT
     ATC ATA TTC CTC TTC ATC CTG CTA TGC CTC ATC TTC TTA TTG GTT CTT CTG GAT TAT           300

301  CAA GGT ATG TTG CCC GTT TGT CCT CTA ATT CCA GGA TCA ACA ACA ACC  AGG ACC (AGT) ACG GGA CCC
     CAA GGT ATG TTG CCC GTT TGT CCT CTA ATT CCA GGA TCA ACA ACA AGA ACC (AGT) ACG GGA CAA       360

361  TGC AAA ACC TGC ACG ACT CCT GCT CAA  GGA AAC TCT ATG TTT CCC  TCC TGT TGC TGT ACA
     TGC AAA ACC TGC ACG ACT CCT GCT CAA (GGC) AAC TCT ATG TTT CCC (TCA) TGT TGC TGT ACA       420

421  AAA CCT ACG GAT GGA AAC TGC ACC TGT ATT CCC ATC CCA  TCA TCC TGG GCT TTC GCA AAA
     AAA CCT ACT ACG GAT GGA(AAT) TGC ACC TGT ATT CCC ATC CCA TTG TCC TGG GCT TTC GCA AAA      480

481  TAC CTA TGG GAG TGG GCC TCA GTC CGT TTC TCT TGG CTC AGT TTA CTA GTG CCA TTT GTT
     TAC CTA TGG GTG TGG GCC TCA GTC CGT TTC TCT TGG CTC AGT TTA CTA GTG CCA TTT GTT       540

541  CAA TGG TTC GTA GGG CTT TCC CCA ACT GTT TGG CTT TCA GCT ATA TGG ATG ATG TGG TAT
     CGG TGG TTC GTA GGG CTT TCC CCA ACT GTT TGG CTT TCA GCT ATA TGG 588                   600

601  TGG GGG CCA AGA CTG TAC TCC ATC GTT AGT CCC TTT ATC CCG CTA CCA ATT TTC TTT           660

661  TGT CTT TGG GTA TAC ATT  678
```

Fig. 4  Nucleotide sequence of the S gene of the novel HBV variant HDB 05:
(nt 127 to nt 588) of the HBV surface antigen-encoding genome.
Only the nucleotide differences which lead to a change in the amino
acid sequence are printed in bold.

```
127  GGG GGA TCA CCC GTG TGT CTT GGC CAA AAT TCG CAG TCC CCA ACC TCC AAT CAC  180
181  TCA CCA ACC TCC TGT CCT CCA ATT TGT CCT GGT TAT CGC TGG ATG TGT CTG CGG CGT TTT  240
241  ATC ATA TTC CTC TTC ATC CTG CTG CTA TGC CTC ATC TTC TTA TTG GTT CTT CTG GAT TAT  300
301  CAA GGT ATG TTG CCC GTT TGT CCT CTA ATT CCA GGA TCA ACA AGA ACC AGT ACG GGA CAA  360
361  TGC AAA ACC TGC ACG ACT CCT GCT CAA GGC AAC TCT ATG TTT CCC TCA TGT TGC TGT ACA  420
421  AAA CCT ACG GAT GGA AAT TGC ACC TGT ATT CCC ATC CCA TTG TCC TGG GCT TTC GCA AAA  480
481  TAC CTA TGG GTG TGG GCC TCA GTC CGT TTC TCT TGG CTC AGT TTA CTA GTG CCA TTT GTT  540
541  CGG TGG TTC GTA GGG CTT TCC CCC ACT GTT TGG CTT TCA GCT ATA TGG  588
```

Fig. 5  S gene nucleotide sequence (nt 127 to 588) and corresponding amino acid sequence (aa 43 to 196) of the novel HBV variant HDB 05 (amino acids which are substituted as compared with the HBV adw wild type are printed in bold and underlined)

```
                                                                                                      180
     127 GGG GGA TCA CCC GTG TGT CTT GGC CAA AAT TCG CAG TCC CCA ACC TCC AAT CAC
      aa 43  G   G   S   P   V   C   L   G   Q   N   S   Q   S   P   T   S   N   H          60
181  TCA CCA ACC TCC TGT CCT CCA ATT TGT CCT GGT TAT CGC TGG ATG TGT CTG CGG CGT TTT        240
      S   P   T   S   C   P   P   I   C   P   G   Y   R   W   M   C   L   R   R   F         80
241  ATC ATA TTC CTC TTC ATC CTG CTA TGC CTC ATC TTC TTA TTG GTT CTT CTG GAT TAT            300
      I   I   F   L   F   I   L   L   C   L   I   F   L   L   V   L   L   D   Y            100
301  CAA GGT ATG TTG CCC GTT TGT CCT CTA ATT CCA GGA TCA ACA ACA ACC AGT ACG GGA CAA        360
      Q   G   M   L   P   V   C   P   L   I   P   G   S   T   R   T   S   T   G   Q        120
361  TGC AAA ACC TGC ACG ACT CCT GCT CAA GGC AAC TCT ATG TTT CCC TCA TGT TGC TGT ACA        420
      C   K   T   C   T   T   P   A   Q   G   N   S   M   F   P   S   C   C   C   T        140
421  AAA CCT ACG GAT GAA AAT TGC ACC TGT ATT CCC ATC CCA TTG TCC TGG GCT TTC GCA AAA        480
      K   P   T   D   E   N   C   T   C   I   P   I   P   L   S   W   A   F   A   K        160
481  TAC CTA TGG GTG TGG GCC AGT GTC CGT TCT CTT TGG CTC AGT TTA CTA GTG CCA TTT GTT        540
      Y   L   W   V   W   A   S   V   R   F   S   W   L   S   L   L   V   P   F   V        180
541  CGG TGG TTC GTA GGG CTT TCC CCC ACT GTT TGG CTT TCA GCT ATA TGG                        588
      R   W   F   V   G   L   S   P   T   V   W   L   S   A   I   W                       aa 196
```

The following aa are substituted (x) in the HDB 05 variant as compared with the HBV adw wild type: T 115 (R), P 120 (Q), S 154 (L), E 164 (V) (all in the region of the a determinant) and Q 181 (R) (not in the region of the a determinant).

Fig. 6 Comparison of the amino acid sequences of the a determinant (aa 100 to aa 180) of the novel variant HDB 05 (lower row) and of the HBV adw wild type (upper row)

```
101  Q  G  M  L  P  V  C  P  L  I  P  G  S  T  T  T  P     120
     Q  G  M  L  P  V  C  P  L  I  P  G  S  T  R  T  Q

121  C  T  K  T  C  T  T  P  A  Q  G  N  S  M  F  P  C  T  140
     C  T  K  T  C  T  T  P  A  Q  G  N  S  M  F  P  C  T

141  K  P  T  D  D  G  N  C  T  C  I  P  I  P  S  S  W  A  F  A  K  160
     K  P  T  D  D  G  N  C  T  C  I  P  I  P  L  S  W  A  F  A  K

161  Y  L  W  E  W  A  S  V  R  F  S  W  L  S  L  L  V  P  F  V  180
     Y  L  W  Y  W  A  S  V  R  F  S  W  L  S  L  L  V  P  F  V

181  Q  W  F  V  G  L  S  P  T  V  190
     R  W  F  V  G  L  S  P  T  V
```

The following aa are substituted (x) in the HDB 05 variant as compared with the HBV adw wild type:

T 115 (R), P 120 (Q), S 154 (L), E 164 (V)   (all in the region of the a determinant) and Q 181 (R) (not in the region of the a determinant)

SURFACE PROTEIN (HBSAG) VARIANT OF THE HEPATITIS B VIRUS

This application is the United States national phase of International Application No. PCT/EP2004/006515, filed on Jun. 17, 2004, which was published on Dec. 29, 2004, as WO2004/113369, and which claims priority to German Application No. 103 28 080.4, filed on Jun. 20, 2003, each of which are incorporated by reference herein.

The invention relates to sequences of a novel mutant or variant of the hepatitis B surface antigen (HBsAg) and D to methods for detecting this genomic and protein variant as well as antibodies in patient samples which are directed against it.

The novel sequences lead to 5 amino acid substitutions, which have not yet been disclosed in the prior art, in the hepatitis B surface antigen, HBsAg, i.e. in amino C) acid positions 115 to 181 of the amino acid sequence of the surface antigen, with 4 substitutions being located in the region of the a determinant (aa 101 to aa 180) and 1 substitution in the direct vicinity thereof (aa 181).

The invention also relates to immunochemical detection methods for simultaneously detecting this novel HBV variant together with known variants/subtypes, as well as to the use of the novel sequences in combination with known sequences for simultaneously detecting HBV-specific antibodies. The antigen or antibody determination can in each case be carried out in a test assay which differentiates or does not differentiate.

Finally, the invention also relates to the detection of the corresponding nucleic acids with the aid of nucleic acid tests (e.g. polymerase chain reaction, PCR) using suitable primers, as well as to the use of the novel amino acid sequences for producing vaccines.

As is known, the hepatitis B virus is the agent responsible for a large number of disease courses, ranging from mild inapparent infections through to liver inflammations which are caused by viral infections (viral hepatites), which are chronically active and which take a fulminating course.

With an estimated 400 million persons being affected, chronic infection with HBV constitutes a global health problem (Lee, N. Engl. J. Med. 337; 1733-1745 (1997)).

Active immunization (stimulating the antibody response by administering antigen) and passive immunization (produced by injecting preformed antibodies) are regarded as being the most suitable prophylaxis for the HBV infection which can frequently be encountered world-wide.

HBV belongs to the Hepadna viruses and constitutes a virus particle having a diameter of 42 nm which consists of a core and an envelope. The genome of the virus is a double-stranded, circular DNA sequence of about 3200 nucleotides which encode at least six different viral genes (Tiollais et al., Nature 317: 489-495 (1985)).

Four open reading frames are available for forming the viral protein.

The S gene contains the information for the HBV surface antigen (HBsAg), which is also termed small protein (S). In addition, there are also larger forms which are designated large protein (L) and middle protein (M). All three proteins possess in common the S-HBsAg sequence comprising 226 amino acids (Gerlich et al., Viral Hepatitis and Liver Disease, Hollinger et al., William-Wilkens, Baltimore, Md., pages 121-134 (1991)). The protein regions upstream of the small HBs are also termed pre-S1 and pre-S2, comprise 108 and 55 amino acids, respectively, and are both present in the L protein (389 amino acids), while the M protein only comprises pre-S2 together with S antigen (281 amino acids). The pre-S proteins exhibit different degrees of glycosylation and carry the receptors for recognizing the liver cells. Unless otherwise indicated, the amino acid positions in this application refer to the S-antigen (226 aa) without pre-S1 region and without pre-S2 region.

The C gene carries the information for the nucleocapsid protein hepatitis B core antigen (HBcAg). The translation of this protein can already start in the pre-C region and leads to the formation of hepatitis B e antigen (HBeAg). The folding and immunogenicity of HBeAg differs from that of HBcAg. In contrast to HBcAg, HBeAg occurs in free form in serum and, in connection with positive detection, is regarded as an indicator of the formation of HBcAg and consequently of the formation of infectious viral particles.

The reverse transcription DNA polymerase which is present in the virus particle is encoded by the P gene, and the possibility is debated of the transactivator X gene having a causative role in the development of HBV-associated primary liver cell carcinomas.

The viral replication cycle of HBV includes an intracellular pregenomic RNA which is reverse transcribed, in the viral nucleocapsid, into the DNA. Since the reverse transcriptase DNA polymerase which is intrinsic to the HBV does not possess any proof-reading capability, incorrect nucleotides are incorporated at a relatively high frequency. As a consequence, HBV exhibits a mutation rate which, at approx. 1 nucleotide/10 000 bases/infection year, corresponds to about 10 times the rate exhibited by other DNA viruses (Blum, Digestion 56: 85-95 (1995); Okamoto et al., Jpn. J. Exp. Med. 57: 231-236 (1987)).

In addition, deletions and insertions also occur quite frequently (Carman et al., Lancet 341: 349-353 (1993)).

The resulting variability of HBV is manifested, inter alia, in the occurrence of 9 serologically defined subtypes (Couroucé et al., Bibliotheca Haematologica 42:1 (1976) and a total of at least 6 different genotypes, which are designated A to F (FIG. 1) and are dispersed geographically. (Norder et al., J. Gen. Virol. 73: 3141-3145 (1992), Norder et al., Virology 198: 489-503 (1994)).

In addition, a number of mutants in which 1 amino acid or more has/have been substituted, or is/are missing or supernumerary, have been described.

Aside from mutations which take place naturally (Cooreman et al., Hepatology 30: 1287-1292 (1999)), administering HBV immunoglobulins and/or an antiviral therapy (e.g. using lamivudine) can exert a selection pressure which leads to an increase in the occurrence of what are termed escape mutants and can markedly increase the probability of the appearance of HBV mutants (Terrault et al., Hepatology 28: 555-561 (1998); Tillmann et al., Hepatology 30: 244-256 (1999); Hunt et al., Hepatology 31: 1037-1044 (2000).

Not all HBV mutations result in replication-capable viruses and there is frequently coexistence with replication-capable virus, a situation which also limits the precision of the sequencing of isolated DNA or even leads to the failure of PCR, cloning procedures and subsequent sequencing to recognize altered sequences when these latter make up quantitatively less than 10% of the total DNA (Cooreman et al., J. Biomed. Sci. 8: 237-247 (2001).

It is consequently advantageous to isolate mutants, with the subsequent identification and characterization of individual mutants possibly leading to improved vaccines and diagnostic agents.

After an infection with HBV, the immune response is principally directed against what is termed the a determinant, as a region of the S protein which is common to all hepatitis B viruses, which region is located on the surface of the virus particles (Gerlich et al., see above) and constitutes the most heterogeneous part of the B cell epitopes of the S gene.

According to the present state of knowledge, a total of at least 5 partially overlapping epitopes on the a determinant between amino acid positions 101 and 180 are assumed to be binding sites for antibodies (FIGS. 1 and 2), as has been demonstrated by using monoclonal antibodies (Peterson et al., J. Immunol. 132: 920-927 (1984)).

These epitopes are chiefly complex conformational epitopes which are stabilized by several disulfide bridges. Some sequence epitopes, which can be produced using synthetically prepared cyclic peptide structures, are also present.

99% of so-called "protective antibodies", which circulate in serum after a natural infection with HBV, are directed against the very immunogenic a determinant of the HBV (Jilg, Vaccine 16: 65-68 (1998).

The widespread use of immunization with vaccines which have either been isolated from human serum or prepared recombinantly, and the administration of hepatitis B immunoglobulins which contain human HBV-specific antibodies, are based on this fact. Both prophylactic strategies are based on the neutralizing effect which HBs-specific antibodies display after binding to the "a loop epitope" (Carman et al., Hepatology 24: 489-493 (1996), Muller et al., J. Hepatol. 13: 90-96 (1991) and Samuel et al., N. Engl. J. Med. 329: 1842-1847 (1993)).

In a similar manner, diagnostic agents which are widely used nowadays are based on the binding of a determinant-specific antibodies with epitopes of the a determinant.

Thus, in the case of the HBsAg determination, using immunochemical determination methods, which is employed world-wide in the field of blood donation, HBV surface antigen which is circulating in the serum of donors is detected using antibodies (of polyclonal or monoclonal origin) which are directed against the a determinant and, if the result is positive, the relevant donated blood is discarded in order to prevent iatrogenic HBV infections due to HBV-contaminated blood. Another application of the HBsAg determination lies in detecting an existing acute HBV infection. Conversely, a positive result when determining HBs-specific antibodies (anti-HBs) in the blood of test subjects demonstrates that either a natural infection has taken its course or that a vaccination which has been carried out has been successful.

Finally, nucleic acid testing, e.g. by means of the polymerase chain reaction (PCR), is also based on using primers (starters) which are specific for the HBV nucleotides.

Due to the central role which the a determinant plays in active immunization (vaccination with HBV antigen), passive immunization (protection by means of HBV-specific immunoglobulins), detection of the success of a vaccination or of an HBV infection which has taken place (both by means of determining HBsAg-specific antibodies, i.e. anti-HBs) and, finally, safety in the field of blood donation (HBsAg determination and PCR), it is understandable that the appearance of mutants, and also new variants, is followed with great attention in specialist circles.

As a consequence, novel mutants and/or variants which were altered in the a determinant of the HBV, but which were capable of replication, could be of interest both in connection with prophylaxis and in connection with diagnosis (Brind et al., J. Hepatol. 26: 228-235 (1997), Fischer et al., Transplant Proc. 31: 492-493 (1999), Ghany et al., Hepatology 27: 213-222 (1998), Protzer-Knolle et al., Hepatology 27: 254-263 (1998), Carman et al., Gastroenterology 102: 711-719 (1992) and Coleman et al., WO 02/079217 A1, (2002)).

While there is no sharp differentiation of variants and mutants of HBV, a proposal in this regard is applied widely (Carman, J. Viral Hepat. 4 (suppl. 1): 11-20 (1997).

According to this proposal, the designation "variant" should be used for naturally occurring subtypes which appear without any known interference due to selection pressure (antiviral therapy and/or immunoglobulin administration) and exhibit a geographic dispersion pattern.

The characterization and subsequent classification of the subtypes is effected using monoclonal antibodies and is based on a change in the reaction patterns due to one or a few amino acid(s) being substituted. Amino acid positions 122 and 160 of the most widespread HBV sequence: aa 122 and aa 160=lysine, K, constitute the basis for the classification.

All the serotypes contain the group-specific a determinant while the aa 122 and, in addition, 133 and 134 determine the d or r subtype and aa 160 determines membership of the w or r subtype. On this basis, HBV subtypes can be roughly divided into adr, adw, ayr and ayw, which subtypes can be further differentiated into at least 9 sub-subtypes: ayw1, ayw2, ayw3, ayw4, ayr, adwr2, adw4, adrq+ and adrq− (Swenson et al., J. Virol. Meth. 33: 27-28 (1991), Blitz et al. J. Clin. Microbiol. 36: 648-651, Ashton-Rickardt et al., J. Med. Virol. 29: 204-214 (1989)).

Since this classification is based on serologic reactivity, every typing does not necessarily have to denote variability at the amino acid level, for which reason preference is given to genotyping at the S gene level (Ohba et al., Virus Res. 39: 25-34 (1995).

For reasons not yet known, subtypes appear in particular geographic and ethnic patterns.

According to Carman, the designation mutation should be reserved for variants which arise exclusively under selection pressure such as vaccination or antiviral therapy. Many mutations have already been described, with a number of them giving rise to diagnostically incorrect findings (Carman et al., Lancet 345: 1406-1407); the aa substitutions which are mentioned below are cited as examples of these mutations:

| Consensus: | aa Position | Mutant: |
|---|---|---|
| I | 110 | V |
| P | 111 | T |
| T | 114 | S |
| T | 116 | S |
| P | 120 | T/S |
| T | 123 | A/N |
| I/T | 126 | A/S |
| Q | 129 | H/R |
| K/M | 133 | L |
| T | 143 | M/L |
| D | 144 | H/A/E |
| G | 145 | R/A |
| A | 157 | R | and also cysteine substitutions in aa positions 107, 124, 137, 147 & 149.

(Coleman, see above; Okamoto et al., Pediatr. Res. 32: 264-268 (1992); Zhang et al., Scand. J. Infect. Dis. 28: 9-15 (1996); Zuckermann et al., Lancet 343: 737-738 (1994)).

Surprisingly, an atypical reaction pattern of hepatitis markers was found in a sample taken from a patient from France (internal number: 119617) who had contracted inflammation of the liver.

Aside from the clinical picture involving an increase in the liver values which were typical for such an infection, IgM class hepatitis core antibodies which were detected also indicated an acute HBV infection, without, however, HBsAg being detected when using an approved high-performance HBsAg ELISA.

A PCR which was carried out surprisingly gave a positive result with the sample, and sequencing led, entirely unexpectedly, to the nucleotide sequence depicted in FIGS. 3 and 4 and to the amino acid sequence depicted in FIGS. 5 and 6, which both unexpectedly led to the substitution pattern described.

It is clear from these sequences that it is, entirely unexpectedly, not a matter of a point mutation, i.e. the substitution of a few nucleotides, and not a matter, either, of a subtype which might possibly be characterized serologically, since a total of n=5 amino acids in the region from aa 115 to 181 are substituted as compared with the A genotype. In view of the frequency of the amino acid substitutions, it is to be assumed, unexpectedly, that it is a matter of a new mutant or that the mutations are so pronounced that the consequence has more likely to be described as being a new variant, which is designated HDB 05 variant in that which follows.

Analysis of the best agreement of the amino acid sequence of the a determinant with known sequences points to genotype A (FIG. 1), subtype adw (FIG. 2), from which, however, the new variant surprisingly differs in 4 aa positions. The 2 adjacent substitutions in the region between aa 115 and 120 and between aa 154 and 164 and the aa position #181 in the direct vicinity of the a determinant, in accordance with FIGS. 1, 5 and 6, constitute the most-prominent feature.

Since it is known that epitopes on the a determinant are occasioned structurally, that is can be present as what are known as conformational epitopes, it seems likely that the immunogenicity, and also the ability of antibodies to bind to the a determinant, can be influenced by the amino acid substitution in position #181.

Finally, and entirely unexpectedly, identity was observed between the nucleotide and amino acid sequences of serum sample #119617 and the corresponding analytical results from another independent serum sample from Austria (internal number: 118457), which likewise originates from a patient who had contracted inflammation of the liver. It can be concluded from this that HDB 05 is a replication-capable and infectious mutant or variant of HBV which may have become disseminated to some degree.

The present invention therefore relates to an oligopeptide or polypeptide which comprises an amino acid sequence which has at least 94% identity with SEQ ID NO: 13. The amino acid sequence shown in SEQ ID NO: 13 corresponds to amino acid positions 111 to 185 of the S antigen of hepatitis B, which antigen has a total length of 226 amino acids. Preferred embodiments relate to an oligopeptide or polypeptide which comprises an amino acid sequence which has at least 95%, at least 96%, at least 97%, at least 98% or at least 99% identity with SEQ ID NO: 13.

The invention also relates to an oligopeptide or polypeptide which comprises an amino acid sequence which has at least 97%, at least 98% or at least 99% identity with SEQ ID NO: 12. The amino acid sequence shown in SEQ ID NO: 12 corresponds to amino acid positions 43 to 196 of the S antigen of the hepatitis B virus, which antigen has a length of 226 amino acids.

The invention also relates to an oligopeptide or polypeptide which comprises an amino acid sequence which has at least 94%, at least 95%, at least 96%, at least 97%, at least 98% or at least 99% identity with SEQ ID NO: 14. The amino acid sequence depicted in SEQ ID NO: 14 corresponds to amino acid positions 111 to 170 of the S antigen of the hepatitis B virus, which antigen has a length of 226 amino acids.

The skilled person is familiar per se with the method for determining the identity between two amino acid sequences, which method can be carried out using customary computer programs. The identity is preferably determined using the "Bestfit" computer program from the Genetics Computer Group (Madison, Wis.). The parameters are used in the standard (default) settings. Preference is given to using the program version which was current on the priority date of the present application. A high percentage identity means that the two sequences exhibit a high degree of correspondence, identity or equivalence.

The oligopeptide or polypeptide according to the invention can also comprise an amino acid sequence in which from 0 to 4 amino acids are substituted, deleted or inserted as compared with SEQ ID NO: 13. From 0 to 3 or from 0 to 2 amino acids, or 1 amino acid, can also be substituted, deleted or inserted in the amino acid sequence as compared with SEQ ID NO: 14. Substitutions can also affect the amino acid positions which correspond to positions 115, 120, 154, 164 and/or 181 of the S antigen of HBV.

The oligopeptide or polypeptide according to the invention can also comprise an amino acid sequence in which from 0 to 3 amino acids are substituted, deleted or inserted as compared with SEQ ID NO: 14. From 0 to 2 amino acids, or 1 amino acid, can also be substituted, deleted or inserted in the amino acid sequence as compared with SEQ ID NO: 14. Substitutions can also affect the amino acid positions which correspond to positions 115, 120, 154, 164 and/or 181 of the S antigen of HBV.

The oligopeptide or polypeptide according to the invention can also comprise an amino acid sequence in which from 0 to 4 amino acids or from 0 to 3 or from 0 to 2 amino acids, or 1 amino acid, are substituted, deleted or inserted as compared with SEQ ID NO: 12.

The oligopeptide or polypeptide of the invention can also comprise an amino acid sequence which is a constituent sequence of SEQ ID NO: 12 containing at least 5 consecutive amino acids of SEQ ID NO: 12, with the constituent sequence at least including one of the positions 73, 78, 112, 122 and 139 of SEQ ID NO: 12. These amino acid positions correspond to positions 115, 120, 154, 164 and 181 of the S antigen of HBV. The constituent sequence preferably comprises at least 6, more preferably at least 7, most preferably at least 8, consecutive amino acids of the amino sequence shown in SEQ ID NO: 12. In other embodiments, the constituent sequence comprises at least 9, at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 100 consecutive amino acids of the amino acid sequence shown in SEQ ID NO: 12.

The constituent sequence preferably includes two, three, four, or all five, of the positions 73, 78, 112, 122 and 139 of SEQ ID NO: 12.

The oligopeptide or polypeptide according to the invention can also comprise a fragment of SEQ ID NO:12, wherein the fragment of SEQ ID NO:12 comprises at least one of the following sequences:

(i) a sequence of at least 8 consecutive amino acids that includes amino acid position 73 of SEQ ID NO:12 and is found within positions 66-80 of SEQ ID NO:12;

(ii) a sequence of at least 6 consecutive amino acids that includes amino acid position 78 of SEQ ID NO:12 and is found within positions 73-83 of SEQ ID NO:12;

(iii) a sequence of at least 6 consecutive amino acids that includes amino acid position 112 of SEQ ID NO:12 and is found within positions 107-117 of SEQ ID NO:12;

(iv) a sequence of at least 30 consecutive amino acids that includes amino acid position 122 of SEQ ID NO:12 and is found within positions 93-151 of SEQ ID NO:12; and (v) a sequence of at least 6 consecutive amino acids that includes amino acid position 139 of SEQ ID NO:12 and is found within positions 134-144 of SEQ ID NO:12

The polypeptide according to the invention can also comprise a fragment of an HBs antigen of a hepatitis B virus, with the fragment having a length of at least 5 amino acids, the HBs antigen possessing arginine at position 115, glutamine at position 120, leucine at position 154, valine at position 164 and/or arginine at position 181, and the fragment comprising arginine 115, glutamine 120. The oligopeptide or polypeptide can include one, two, three, four leucine 154, valine 164 and/or arginine 181 or five of these specific amino acid residues.

The shortest length of the oligopeptides or polypeptides according to the invention is 5, preferably 6, more preferably 7, most preferably 8, amino acids. The total length of the oligopeptide or polypeptide is as a rule from 5 to 1000 aminoacids, preferably from 6 to 500 amino acids, more preferably from 7 to 300 amino acids, most preferably from 8 to 200 amino acids. The oligopeptides or polypeptides can also contain foreign amino acids which are not encoded by the genome of a hepatitis B virus. Thus, it is possible for amino acids which facilitate coupling solid phases or make possible coupling to labeling substances to be present. It is possible for amino acids which have arisen as a result of the cloning, and which have been concomitantly expressed in association with the recombinant expression, to be present. Finally, the oligopeptide or polypeptide according to the invention can be a fusion protein which, in addition to HBV-derived amino acids, contains a fusion partner, e.g. a tag sequence which facilitates purification, or a protein moiety which increases solubility and/or the yield in association with recombinant expression. Fusion partners of this nature are known per se to the skilled person.

In another embodiment, the oligopeptides or polypeptides do not contain any foreign amino acids which are not encoded by the genome of an HBV. Correspondingly, these oligopeptides or polypeptides are composed of one of the amino acid sequences described above and/or in the claims.

The oligopeptide or polypeptide according to the invention is preferably immunogenic, i.e. it is able to induce an antibody response in a mammalian organism. The oligopeptide or polypeptide customarily contains at least one antigenic determinant or at least one epitope. In a special embodiment, the oligopeptide or polypeptide contains an epitope which is not present in other HBV variants, e.g. in genotype A, subtype adw.

The oligopeptide or polypeptide preferably comprises one of the amino acid sequences SEQ ID NO: 12; SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22.

Another aspect of the invention is an immunogenic peptide or a mixture of immunogenic peptides which contain one or more of the oligopeptides or polypeptides which are described in this application. The immunogenic peptides or the immunogenic mixture can contain the oligopeptide(s) or polypeptide(s) on its/their own or in combination with known HBV immunogens.

The present invention also relates to nucleic acid molecules which are derived from the genome of the novel HBV variant HDB 05 or mutants thereof, in particular nucleic acid molecules which are derived from the gene which encodes HSbAg.

The invention therefore relates, for example, to an oligonucleotide or polynucleotide which comprises a nucleotide sequence which has at least 98% identity with SEQ ID NO: 2. The nucleotide sequence SEQ ID NO: 2 encodes the amino acid sequence SEQ ID NO: 13.

Preferred embodiments relate to an oligonucleotide or polynucleotide which comprises a nucleotide sequence which has at least 99% identity with SEQ ID NO: 2.

The invention also relates to an oligonucleotide or polynucleotide which comprises a nucleotide sequence which has at least 99% identity with SEQ ID NO: 1. The nucleotide sequence SEQ ID NO: 1 encodes the amino acid sequence SEQ ID NO: 12.

In this case, identity is defined as the degree of identity between two strands of two DNA segments. The identity is expressed as a percentage, with the number of identical bases in two sequences which are to be compared being divided by the length of the shorter sequence and multiplied by 100 (Smith et al., Adv. Appl. Mathem. 2: 482-489 (1981).

The skilled person is familiar with the method for determining the identity between two amino acid sequences and this method can be carried out using customary computer programs. The identity is preferably determined using the "Bestfit" computer program from the Genetics Computer Group (Madison, Wis.). The parameters are used in the standard (default) settings. Preference is given to using the program version which was current on the priority date for the present application. A high percentage identity means that the two sequences exhibit a high degree of correspondence, identity or equivalence.

This assessment can also be applied to amino acid sequences of peptides and proteins (Dayhoff, Atlas of Protein Sequences and Structure, M. O. Dayhoff ed. 5 Suppl. 3: 353-358, Nat. Biom. Res. Found., Washington D.C., USA, Gribskov, Nucl. Acids Res. 14(6): 6745-66763 (1986)).

The invention furthermore relates to an oligonucleotide or polynucleotide which comprises a nucleotide sequence in which from 0 to 4 nucleotides are substituted, deleted or added as compared with SEQ ID NO: 2. From 0 to 3 or from 0 to 2 nucleotides, or 1 nucleotide, can also be substituted, deleted or inserted in the nucleotide sequence as compared with SEQ ID NO: 2.

The oligonucleotide or polynucleotide according to the invention can also comprise a nucleotide sequence which is a constituent sequence of SEQ NO:1 containing at least 8 consecutive nucleotides of SEQ ID NO:1, with the constituent sequence including at least one of the positions 218, 233, 335, 365 and 416 of SEQ ID NO:1. The constituent sequence preferably comprises at least 9, more preferably at least 10, most preferably at least 12, consecutive nucleotides of the nucleotide sequence shown in SEQ ID NO:1. In other embodiments, the constituent sequence comprises at least 15, at least 18, at least 20, at least 25, at least 30, at least 35, at least 40, at least 45, at least 50, at least 60, at least 70, at least 80, at least 90, at least 100, at least 120, at least 150, at least 175, at least 200, at least 250 or at least 300 consecutive nucleotides of the nucleotide sequence shown in SEQ ID NO:1.

The constituent sequence preferably includes two, three, four, or all five of the positions 218, 233, 335, 365 and 416 of SEQ ID NO: 1.

In another embodiment, the oligonucleotide or polynucleotide comprises a nucleotide sequence which hybridizes, under stringent conditions and preferably specifically, with a polynucleotide which is complementary to the sequence SEQ ID NO: 1. In yet other embodiments, the oligonucleotide or polynucleotide comprises a nucleotide sequence which hybridizes, under stringent conditions and preferably specifically, with a polynucleotide which is complementary to the sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and/or SEQ ID NO: 11. The skilled person is familiar per se with methods for determining whether a given oligonucleotide or polynucleotide hybridizes with another polynucleotide. The following conditions constitute a special example of "stringent conditions": a) 16-hour incubation at 42° C. in a solution containing 50% formamide, 5×SSC (150 mM NaCl, 15 mM trisodium citrate), 50 mM sodium phosphate, pH 7.6, 5×Denhardt's solution, 10% dextran sulfate and 20 µg of denatured, sheared salmon sperm DNA/ml; b) subsequent washing in 0.1×SSC at approximately 65° C. Hybridization and washing conditions are known per se to the skilled person and are specified, by way of example, in Sambrook et al., Molecular Cloning: A Laboratory Manual, Second Edition, Cold Spring Harbor, N.Y., (1989). A nucleotide sequence hybridizes specifically with a given polynucleotide when it does not hybridize, or hybridizes much more weakly, with other nucleotide sequences. In the present case, this can mean that the nucleotide sequence does not hybridize, or only hybridizes weakly, with HBsAg-encoding polynucleotides from conventional HBV variants (e.g. genotype A, subtype adw).

The invention also relates to an oligonucleotide or polynucleotide which comprises a nucleotide sequence which encodes an oligopeptide or polypeptide according to the invention as, described in this application.

Another aspect of the invention is an oligonucleotide or polynucleotide which comprises a nucleotide sequence which is complementary to the above-described nucleotide sequences.

The shortest length of the oligonucleotides or polynucleotides according to the invention is 6, preferably 8, more preferably 10, most preferably 12, nucleotides. The total length of the oligonucleotide or polynucleotide is as a rule from 6 to 3000 nucleotides, preferably from 6 to 1500 nucleotides, more preferably from 8 to 900 nucleotides, most preferably from 8 to 600 nucleotides. The oligonucleotides or polynucleotides can also contain nucleotides which are not derived from the genome of a hepatitis B virus. Thus, it is possible for nucleotides which encode particular amino acids which are intended to fulfill desired functions, as described above, to be present. It is possible for nucleotides which have arisen because of the cloning, e.g. in order to insert particular cleavage sites, to be present. Finally, the oligonucleotide or polynucleotide according to the invention can encode a fusion protein which, in addition to HBV-derived amino acids, contains a fusion partner, e.g. a tag sequence which facilitates purification, or a protein moiety which increases solubility and/or the yield in association with recombinant expression. Fusion partners of this nature, and the DNA encoding them, are known per se to the skilled person.

Preferred oligonucleotides or polynucleotides of the present invention comprise a nucleotide sequence which is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11.

The polynucleotides according to the invention can also be labeled, for example by means of a fluorescent label or a radioactive label. Polynucleotides of this nature can advantageously be employed in a hybridization reaction or a polymerase chain reaction (PCR).

The invention also relates to a vector or a plasmid which contains an oligonucleotide or polynucleotide according to the invention. The plasmid can, for example, be a cloning vector which is used to replicate the nucleic acid in host cells or to make available particular restriction cleavage sites. Expression vectors are vectors which enable the cloned nucleic acid to be expressed in host cells. Various prokaryotic or eukaryotic cells can be host cells. Examples of prokaryotic host cells are bacterial cells such as E. coli cells. The expression vectors according to the invention can contain particular control elements such as promoters or sites for binding repression factors. In another embodiment, the expression vectors contain a nucleic acid segment which encodes a part of a fusion protein.

The invention likewise relates to a cell, e.g. a host cell, which harbors a polynucleotide according to the invention, plasmid according to the invention or a vector according to the invention. The host cells can be cultured under suitable conditions such that transcription of the nucleic acid which is present, and subsequent translation, takes place. The invention also relates to a method for preparing a polypeptide, in which method a polynucleotide, a plasmid or an expression vector of the invention is introduced into host cells and the host cells are cultured under conditions which lead to the polypeptide being expressed. Where appropriate, the polypeptide can subsequently be isolated from the host cells. The polypeptide is preferably prepared in bacteria, most preferably in E. coli cells. Suitable means and conditions for the culture are described, for example, in Ausubel et al. (1993) "Current Protocols in Molecular Biology". The expressed polypeptide is isolated using methods which are known per se to the skilled person. Various methods for purifying proteins are described, for example, in Scopes R. (1994) "Protein Purification: Principles and Practice" (3rd edition) Springer Verlag.

However, the polypeptides and peptides of the present invention can also be prepared chemically using known methods such as solid phase synthesis. In the same way, the polynucleotides according to the invention can be prepared using known methods of chemical synthesis. Polynucleotide fragments which have been obtained by means of chemical synthesis can then also be linked enzymatically using ligases. The oligonucleotides or polynucleotides according to the invention can also be prepared from known sequences by means of site directed mutagenesis, with point mutations being inserted at particular positions. Methods of this nature are known per se to the skilled person.

Another aspect of the invention is an antibody which binds to an oligopeptide or polypeptide according to the invention. These antibodies can be prepared in a known manner, either using an oligopeptide or polypeptide of the invention, e.g. a peptide having one of the sequences SEQ ID NO: 12 to 22, or using a fragment thereof (Harlow and Lane (1988) Antibodies: A Laboratory Manual; Cold Spring Harbor Laboratory). While the antibodies can be polyclonal or monoclonal antibodies, monoclonal antibodies are preferred. The antibodies are preferably specific antibodies which are directed against the HBsAg of the novel HBV variant but which do not recognize HBsAg from other HBV variants, e.g. genotype A subtype adw. These antibodies can be obtained by identifying peptides which, on the basis of a comparison of the amino acid sequences of the novel HBsAg and HBsAg from known strains, are specific for the novel HBsAg and using these peptides to prepare the antibodies. It is also possible to prepare a mixture of polyclonal antibodies and to deplete this mixture by incubating it with known HBsAg. In another embodiment, the antibody recognizes known HBsAg variants as well as the novel HBsAg. This makes it possible to detect different variants of HBsAg simultaneously.

The antibody of the invention can bind to an oligopeptide or polypeptide which is composed of an amino acid sequence which is selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22. The antibody particularly preferably binds to an oligopeptide or polypeptide which is composed of an amino acid sequence which is selected from the group consisting of SEQ ID NO: 17, SEQ ID NO: 18, SEQ ID NO: 19, SEQ ID NO: 20, SEQ ID NO: 21 and SEQ ID NO: 22. In a special embodiment, the antibody does not bind to the a determinants of the known HBV genotypes A, B, C, D, E and F (see FIG. 1). In a special embodiment, the antibody does not bind to the a determinant of HBV genotype A, subtype adw.

The invention furthermore relates to an antiidiotypic antibody which represents an amino acid sequence of an oligopeptide or polypeptide according to the invention. Methods for preparing antiidiotypic antibodies are known per se to the skilled person.

The invention also relates to a test kit for detecting hepatitis B viruses, which kit comprises an oligopeptide or polypeptide according to the invention, an oligonucleotide or polynucleotide according to the invention and/or an antibody according to the invention.

The invention also relates to an immunogenic peptide or a mixture of immunogenic peptides which contains one or more oligopeptide(s) or polypeptide(s) according to the invention on its/their own or in combination with known HBV immunogens.

Another aspect of the invention is a method for detecting a hepatitis B antigen, characterized in that (a) a sample is incubated with an antibody according to the invention under conditions which allow the formation of an antigen-antibody complex; and (b) an antigen-antibody complex which contains the antibody is detected.

It is possible to use monoclonal or polyclonal antibodies (or mixtures or fragments thereof or mixtures of fragments) which react with epitopes of the novel HBV variant to determine the a determinant of the HBV variant according to the invention, in the form of the entire polypeptide sequence or parts thereof, in experimental samples: HBsAg of the HDB 05 variant.

The skilled person is familiar with a large number of determination methods in which immune complexes are formed, or their formation is inhibited, using one or more monoclonal antibody(ies) or polyclonal antibodies (or mixtures thereof or fragments or mixtures of fragments) which is/are specific for the a determinant of the HBV variant.

A special embodiment is the enzyme immunoassay, a possible test principle of which is described below by way of example without, however, restricting the idea of the invention to this principle:

In the very widely used sandwich principle, immobilized antibodies, or fragments thereof, are incubated with the sample under investigation on a suitable support (e.g. microparticles or the surface of wells in a microtitration plate). After excess sample has been removed, HBsAg which is bound to the antibodies is detected by carrying out a further incubation with anti-HBs antibodies (monoclonal or polyclonal or fragments or mixtures of these fragments) which are provided with a probe. The probe employed is frequently an enzyme whose catalytic conversion (after the excess reagent has been removed) of a suitable substrate results in a color reaction which is measured photometrically and whose intensity is proportional to the content of HBsAg which is present in the sample.

Aside from this special embodiment, methods are also known which are homogeneous in nature (i.e. do not required any bound/free separation), which manage entirely without any probe (e.g. agglutination method), which can be evaluated with the naked eye (e.g. radial immunodiffusion), or which makes use of other probes (e.g. radioactive isotopes or chemiluminescence) or several probes (e.g. the biotin/streptavidin system).

All these embodiments correspond to the prior art, such that, in the case of the present invention, "determining HBsAg of the novel HBV variant" is understood as referring to any methods which are suitable for detecting polypeptide sequences or antigens of the novel HBV variant, irrespective of whether the HBsAg of the novel variant is determined on its own or whether it is determined in combination with HBsAg of known a determinants and/or known mutations in the a region.

It is likewise possible, for economic reasons, to combine an HBsAg determination with a method for detecting another analyte (e.g. HIV antigen or the simultaneous determination of HBV variant HBsAg and specific antibodies directed against it) in one test assay (which is differentiating or non-differentiating).

The invention also relates to a method for detecting antibodies which are directed against a hepatitis B antigen, characterized in that (a) a sample is incubated with an oligopeptide or polypeptide according to the invention under conditions which allow the formation of an antigen-antibody complex; and (b) the antibody-antigen complex which contains the oligopeptide or polypeptide is detected.

A special embodiment is the enzyme immunoassay, a possible test principle of which is described below by way of example without, however, restricting the idea of the invention to this principle:

In the very widely used sandwich principle, immobilized epitope-carrying polypeptide or protein sequences are incubated with the sample under investigation on a suitable support (e.g. microparticles or the surface of wells in a microtitration plate). After excess sample has been removed, antibodies which are bound to the epitopes are detected by carrying out a further incubation with epitope-carrying polypeptide or protein sequences which are provided with a probe. The probe employed is frequently an enzyme whose catalytic conversion (after the excess reagent has been removed) of a suitable substrate results in a color reaction which is measured photometrically and whose intensity is proportional to the content of antibody which is present in the sample.

Aside from this special embodiment, methods are also known which are homogeneous in nature (i.e. not require any bound/free separation), which manage entirely without a probe (e.g. agglutination method), which can be evaluated with the naked eye (e.g. radial immunodiffusion) or which make use of other probes (e.g. radioactive isotopes or chemiluminescence) or several probes (e.g. the biotin/streptavidin system).

It is likewise possible for the polypeptide structures of the HBV variant to be represented by antiidiotypic antibodies or, by selecting a suitable test principle, for variant-specific monoclonal or polyclonal antibodies to be used for determining anti-HBs antibodies (in a competitive test format). It is likewise known that, by selecting the test principle, it is also possible to differentiate the immunoglobulin classes (e.g. by means of the "indirect" method using a second class-specific antibody (e.g. IgM- or IgG-specific) possessing any probe or with the aid of what is termed the anti-µ principle (IgMspecific). The methods and materials (incl. probe and polypeptide sequences) naturally have to be adapted to the given aim.

All these embodiments correspond to the prior art, such that, in the case of the present invention, "determining antibodies which are specific for the a determinant of the novel HBD 05 variant" is understood as referring to any methods which are suitable for detecting immunoglobulins and/or immunoglobulin classes directed against the novel HBV variant, irrespective of whether the antibody directed against the novel variant is sought on its own or in combination with antibodies directed against known a determinants and/or known mutations in the a region. In another method, it is possible to detect a hepatitis B nucleic acid. This method is characterized in that (a) a sample is incubated with an oligonucleotide or polynucleotide according to the invention under conditions which allow the selective hybridization of the oligonucleotide or polynucleotide with a hepatitis B nucleic acid in the sample; and (b) it is determined whether polynucleotide duplexes which comprise the oligonucleotide or polynucleotide have been formed.

The hepatitis B nucleic acid can also be detected by (a) incubating a sample with at least one oligonucleotide or polynucleotide according to the invention under conditions which allow the selective hybridization of the oligonucleotide or polynucleotide with a hepatitis B nucleic acid in the sample; (b) carrying out a polymerase chain reaction; and (c) determining whether a nucleic acid has been amplified.

The invention also relates to the use of an oligonucleotide or polynucleotide according to the invention as a primer and/or as a probe. The present nucleotide sequences can be used for preparing primers and/or gene probes, for which reason kits which comprise primers and/or probes for detecting HBV variant-specific nucleic acid, either on its own or in combination with known HBV nucleotide sequences, in samples under investigation are likewise part of the subject matter of the invention.

On the basis of the present nucleotide sequences, it is possible to develop primers which can be used in the polymerase chain reaction (PCR). PCR is a method for amplifying a desired nucleotide sequence of a nucleic acid or of a nucleic acid mixture. In this method, the primers are in each case extended specifically by a polymerase using the desired nucleic acid as the reading frame. Following dissociation from the original strand, new primers are hybridized and once again extended by the polymerase. By repetition of these cycles, the sought-after target sequence molecules are enriched.

With reference to nucleic acid tests (NATs), it is possible to use nucleotide sequences of the present invention to prepare DNA oligomers of 6-8 nucleotides or more which are suitable for use as hybridization probes for detecting the viral genome of the HBV variant which is described in individuals who are possibly carrying the virus variant, or, for example in the field of blood donation, for screening stored blood for the presence of the variant genome, either selectively or in combination with detecting nucleotide sequences of known HBV variants and/or HBV mutants.

It is likewise possible, on the basis of the nucleotide sequences of the novel HBV variant which have been found, to develop corresponding primers which are specific for the novel variant or which are able to detect both the novel variant and variants which are known in the prior art.

The present invention furthermore relates to an isolated hepatitis B virus which possesses an HBs antigen which comprises an amino acid sequence having at least 97%, at least 98% or at least 99%, identity with SEQ ID NO: 12. The HBs antigen of the virus according to the invention preferably comprises the amino acid sequence SEQ ID NO: 12. Finally, the invention also relates to cultures of tissue cells which are infected with the HBV variant according to the invention, as well as the isolated HBV variant itself. An immunogenic preparation which contains the attenuated or inactivated HDB 05 variant of HBV is also part of the subject matter of the invention.

The invention also relates to the use of an oligonucleotide or polynucleotide according to the invention, or of an oligopeptide or polypeptide according to the invention, for producing a pharmaceutical for treating or preventing an HBV infection. In particular, the oligonucleotides or polynucleotides or oligopeptides or polypeptides according to the invention can be used for producing a vaccine against HBV.

In addition, the invention also includes a vaccine which comprises a polypeptide of the present invention and a customary adjuvant (e.g. Freund's adjuvant, phosphate-buffered saline or the like). A vaccine of this nature can be used to stimulate the formation of antibodies in mammals. Similarly, the invention encompasses a particle which comprises a non-variant-specific amino acid sequence which induces particle formation together with an epitope-containing polypeptide which is specific for the HBV variant according to the invention.

The nucleotide sequences of the invention can also be used for preparing antisense oligonucleotides (where appropriate for therapeutic purposes).

Further aspects of the present invention are constituted by the following subject matter items (1) to (21):

(1) Isolated oligonucleotide or polynucleotide having one of the sequences selected from the group consisting of Seq id no: 1 to Seq id no: 11:

```
SEQ ID NO: 1
127 GGGGGATCAC CCGTGTGTCT TGGCCAAAAT TCGCAGTCCC CAACCTCCAA
    TCACTCACCA ACCTCCTGTC CTCCAATTTG TCCTGGTTAT CGCTGGATGT
    GTCTGCGGCG TTTTATCATA TTCCTCTTCA TCCTGCTGCT ATGCCTCATC
    TTCTTATTGG TTCTTCTGGA TTATCAAGGT ATGTTGCCCG TTTGTCCTCT
    AATTCCAGGA TCAACAAGAA CCAGTACGGG ACAATGCAAA ACCTGCACGA
    CTCCTGCTCA AGGCAACTCT ATGTTTCCCT CATGTTGCTG TACAAAACCT
    ACGGATGGAA ATTGCACCTG TATTCCCATC CCATTGTCCT GGGCTTTCGC
    AAAATACCTA TGGGTGTGGG CCTCAGTCCG TTTCTCTTGG CTCAGTTTAC
    TAGTGCCATT TGTTCGGTGG TTCGTAGGGC TTTCCCCCAC TGTTTGGCTT
    TCAGCTATAT GG                                         588

SEQ ID NO: 2
331 CCAGGATCAA CAAGAACCAG TACGGGACAA TGCAAAACCT GCACGACTCCT
    GCTCAAGGCA ACTCTATGTT TCCCTCATGT TGCTGTACAA AACCTACGGA
    TGGAAATTGC ACCTGTATTC CCATCCCATT GTCCTGGGCT TTCGCAAAAT
    ACCTATGGGT GTGGGCCTCA GTCCGTTTCT CTTGGCTCAG TTTACTAGTG
    CCATTTGTTC GGTGGTTCGT AGGG                            555
```

```
SEQ ID NO: 3
331 CCAGGATCAA CAAGAACCAG TACGGGACAA TGCAAAACCT GCACGACTCC
    TGCTCAAGGC AACTCTATGT TTCCCTCATG TTGCTGTACA AAACCTACGG
    ATGGAAATTGC ACCTGTATT CCCATCCCAT TGTCCTGGGC TTTCGCAAAA
    TACCTATGGG TGTGGGCCTC AGTCCGTTTC                          510

SEQ ID NO: 4
331 CCAGGATCAA CAAGAACCAG TACGGGACAA TGCAAAACCT GCACGACTCC
    TGCTCAAGGC AACTCTATGT TTCCCTCATG TTGCTGTACA AAACCTACGG
    ATGGAAATTG CACCTGTATT CCCATCCCAT TGTCCTGGGC TTTCGCAAAA
    TACCTATGGG
    TGTGG                                                     495

SEQ ID NO: 5
331 CCAGGATCAA CAAGAACCAG TACGGGACAA TGCAAAACCT GCACGACTCC
    TGCTCAAGGC                                                390

SEQ ID NO: 6
331 CCAGGATCAA CAAGAACCAG TACGGGACAA                          360

SEQ ID NO: 7
343 AGAACCAGTA CGGGACAATG CAAAACCTGC ACGACTCCTG CTCAAGGCAA
    CTCTATGTTT CCCTCATGTT GCTGTACAAA ACCTACGGAT GGAAATTGCA
    CCTGTATTCC CATCCCATTG TCCTGGGCTT TCGCAAAATA CCTATGGGTG
    TGG                                                       495

SEQ ID NO: 8
343 AGAACCAGTA CGGGACAA                                       360

SEQ ID NO: 9
460 TTGTCCTGGG CTTTCGCAAA ATACCTATGG GTGTGGGCCT CAGTCCGTTT
    CTCTTGGCTC AGTTTACTAG TGCCATTTGT TCGGTGGTTC GTAGGG        555

SEQ ID NO: 10
460 TTGTCCTGGG CTTTCGCAAA ATACCTATGG GTGTGGGCCT CAGTCCGTTT
    C                                                         510

SEQ ID NO: 11
462 TTGTCCTGGG CTTTCGCAAA ATACCTATGG GTGTGG                   495
```

(2) Oligonucleotide or polynucleotide according to (1) which is in each case at least 65% or 66% or 67% or 68% or 69% or 70% or 71% or 72% or 73% or 74% or 75% or 76% or 77% or 78% or 79% or 80% or 81% or 82% or 83% or 84% or 85% or 86% or 87% or 88% or 89% or 90% or 91% or 92% or 93% or 94% or 95% or 96% or 97% or 98% or 99% identical with one of the sequences selected from the group consisting of SEQ ID NO:1 to SEQ ID NO:11.

(3) Oligonucleotide or polynucleotide according to (1) or (2) which hybridizes, under stringent conditions, with an oligonucleotide or polynucleotide which has a sequence which is complementary to one of the sequences selected from the group consisting of Seq id no: 1 to Seq id no: 11.

(4) Isolated oligonucleotide or polynucleotide which encodes HBs antigen of the hepatitis B virus and contains an oligonucleotide or polynucleotide according to one of the subject-matter items (1) to (3).

(5) Fragment of an oligonucleotide or polynucleotide which encodes HBs antigen of the hepatitis B virus, characterized in that the fragment contains an oligopeptide or polypeptide according to one of the subject-matter items (1) to (3).

(6) Isolated oligonucleotide or polynucleotide which encodes the a determinant of the HBs antigen of the hepatitis B virus and contains an oligonucleotide or polynucleotide according to one of the subject-matter items (1) to (3).

(7) Primer which is specific for an oligonucleotide or polynucleotide according to one of the subject-matter items (1) to (6).

(8) Vector which contains at least one oligonucleotide or polynucleotide according to one of the subject-matter items (1) to (5).

(9) Host cell which harbors a vector according to (8).

(10) Oligopeptide or polypeptide which is encoded by an oligonucleotide or polynucleotide according to one of the subject-matter items (1) to (5).

(11) An isolated oligopeptide or polypeptide which has an amino acid sequence which is selected from the group consisting of Seq id no: 12 to Seq id no 22:

```
Seq id no.: 12
 43     G G S P V C L G Q N S Q S P T S N H
     S P T S C P P I C P G Y R W M C L R R F
     I I F L F I L L L C L I F L L V L L D Y
     Q G M L P V C P L I P G S T R T S T G Q
     C K T C T T P A Q G N S M F P S C C C T
     K P T D G N C T C I P I P L S W A F A K
     Y L W V W A S V R F S W L S L L V P F V
     R W F V G L S P T V W L S A I W         196

Seq id no.: 13
111     P G S T R T S T G Q C K T C T T P A
     Q G N S M F P S C C C T K P T D G N C T
     C I P I P L S W A F A K Y L W V W A S V
     R F S W L S L L V P F V R W F V G       185

Seq id no.: 14
111     P G S T R T S T G Q C K T C T T P A
     Q G N S M F P S C C C T K P T D G N C T
     C I P I P L S W A F A K Y L W V W A S V
     R F                                     170

Seq id no.: 15
111     P G S T R T S T G Q C K T C T T P A
     Q G N S M F P S C C C T K P T D G N C T
     C I P I P L S W A F A K Y L W V W       165
```

-continued

```
Seq id no.: 16
111      P G S T R T S T G Q C K T C T T P A
         Q G                                      130

Seq id no.: 17
111  P G S T R T S T G Q                          120

Seq id no.: 18
115      R T S T G Q C K T C T T P A Q G N S
     M F P S C C C T K P T D G N C T C I P I
     P L S W A F A K Y L W V W                    165

Seq id no.: 19
115: R T S T G Q                                  120

Seq id no.: 20
154      P I P L S W A F A K Y L W V W A S V R
     F S W L S L L V P F V R W F V G L            185

Seq id no..:21
154      P I P L S W A F A K Y L W V W A S V R
     F                                            170

Seq id no.: 22
154: P I P L S W A F A K Y L W V W                165
```

(12) An oligopeptide or polypeptide according to (10) or (11) which is in each case at least 65% or 66% or 67% or 68% or 69% or 70% or 71% or 72% or 73% or 74% or 75% or 76% or 77% or 78% or 79% or 80% or 81% or 82% or 83% or 84% or 85% or 86% or 87% or 88% or 89% or 90% or 91% or 92% or 93% or 94% or 95% or 96% or 97% or 98% or 99% identical with one of the sequences selected from the group consisting of SEQ ID NO:12 to SEQ ID NO:22.

(13) An isolated polypeptide corresponding to the sequence of the HBs antigen of the hepatitis B virus, characterized in that it contains an oligopeptide or polypeptide according to one of the subject-matter items (10) to (12).

(14) A fragment of a polypeptide which corresponds to the sequence of the HBs antigen of the hepatitis B virus, characterized in that the fragment contains an oligopeptide or polypeptide according to one of the subject-matter items (10) to (12).

(15) An isolated polypeptide which encodes the a determinant of the HBs antigen of the hepatitis B virus, characterized in that it contains an oligopeptide or polypeptide according to one of the subject-matter items (10) to (12).

(16) A monoclonal or polyclonal antibody which binds to HBs antigen containing an oligopeptide or polypeptide according to one of the subject-matter items (10) to (15) but which does not bind, or at least binds significantly more weakly, to HBs antigen belonging to a hepatitis B wild-type virus.

(17) An antiidiotypic antibody which represents an amino acid sequence according to one of the subject-matter items (10) to (15).

(18) A test kit for detecting or determining, by means of a hybridization reaction, a nucleic acid which is specific for a variant or mutant of the hepatitis B virus using at least one oligonucleotide or polynucleotide according to one or more of the subject-matter items (1) to (7).

(19) A test kit for immunochemically detecting or immunochemically determining an antigen which is specific for a variant or mutant of the hepatitis B virus using at least one monoclonal or polyclonal antibody according to (16).

(20) A test kit for immunochemically detecting or immunochemically determining an antibody directed against a variant or mutant of the hepatitis B virus using at least one oligopeptide or polypeptide according to one of the subject-matter items (10) to (15).

(21) An immunogenic peptide or mixture of immunogenic peptides which contains one or more oligopeptides or polypeptides according to one or more of the subject-matter items (3) and (4) on its own or in combination with known HBV immunogens.

The present invention encompasses an isolated nucleotide sequence which is at least 65% identical with Seq id no: 1 or with a fragment of this sequence depicted in FIGS. 3 and 4 which hybridizes specifically with the complement of SEQ ID NO: 1 to 11.

In addition, the present invention encompasses an isolated nucleotide sequence which encodes the present variant according to the invention of the a determinant of the hepatitis B surface antigen (HBsAg) in the amino acid positions between aa 101 and 180 or leads to a peptide product whose aa sequence is in at least 65% agreement with the SEQ ID NO: 12 depicted in FIGS. 5 and 6 or fragments thereof in accordance with SEQ ID NO: 13 to 22.

The present invention furthermore relates to a vector which comprises one or more of said nucleotide sequences as well as to a host cell which harbors this vector and to a method for preparing a corresponding polypeptide from the a determinant, which method comprises incubating the abovementioned host cell over periods and under conditions which are required for expressing the polypeptide.

The invention also relates to antibodies which react with the a determinant described in SEQ ID NO: 11 to 22, with the binding preferably taking place in the amino acid region aa 115 to 120, aa 154 to 164 or aa 154 to 185. The antibodies can be of polyclonal or monoclonal, animal or human origin.

The invention likewise relates to an isolated HBV variant, with the virus possessing an a determinant which corresponds to the aa sequences at least between position 115 and 120 and/or aa 154 to 164 or aa 154 to 181, ideally to all said regions between 115 and 181.

The present invention also relates to an immunogenic mixture for generating polyclonal or monoclonal antibodies, which mixture comprises the described, isolated HBV or one or more of the described polypeptides.

The invention also encompasses a polynucleotide probe which contains an HBV genome sequence which, by substitution of amino acids, leads to a modified a determinant which is identical with the described aa sequence of the novel HBV variant or is in at least 65% correspondence with it.

The invention also relates to kits for detecting polynucleotides of the HBV variant with the aid of said probe as well as to kits for detecting HBsAg of the variant or individual epitopes thereof and to antibodies which are specific for the variant or epitopes thereof, as well as to the methods for detecting polynucleotides, antigen and antibody, comprising an incubation for forming corresponding complexes and detection of these complexes using suitable methods known to the skilled person.

The embodiments of these kits and detection methods can be designed for the specific and sole detection of nucleotides and antigens of the HBV variant, or of antibodies directed against them, or be supplementary, i.e. permit detection of the variant analyte according to the invention in addition to currently known HBV nucleotides, antigens or antibodies.

In an analogous manner, an immunogenic mixture of polypeptide sequences according to the invention can also be used in combination with known antigens, e.g. for improving the efficacy of the vaccine.

The present invention describes a novel variant of the hepatitis B virus (HBV) which possesses an entirely novel a determinant as a result of amino acid substitutions in the following aa positions of the S-HBsAg sequence. The single-letter code is used for describing the amino acids:

| aa of HDB 05 | aa position | aa of adw/genotype A |
|---|---|---|
| R | 115 | T |
| Q | 120 | P |
| L | 154 | S |
| V | 164 | E |

In addition, arginine (R) is present in place of Gln (O) in position aa 181 of HDB 05:

R 181 Q

These aa substitutions can be attributed to corresponding nucleotide substitutions in the corresponding codons.

The present invention relates to an isolated nucleotide sequence which encodes the a determinant of the virus (FIG. 3 and also Seq id no: 1).

The invention also encompasses nucleotides having at least 65% congruence, preferably at least 75% congruence, and particularly preferably having at least 90% congruence, with the nucleotide sequence of the present invention, or fragments thereof, as well as sequences which are complementary thereto.

The invention also encompasses polypeptides which are encoded by above-described nucleotide sequences, in particular those amino acid sequences which determine the a determinant of the HBsAg, and polypeptides which at least exhibit a similarity of 65%, preferably 75%, and even more preferably 95%, to these sequences.

For the description of the present invention, a nucleotide fragment is understood as being a consecutive sequence of at least 9, preferably 9-15, particularly preferably 15-21, and even very particularly preferably 21-60, nucleotides from the nucleotide sequence of the novel HBV variant, with mixtures of these nucleotide fragments also being assumed.

A polypeptide fragment is understood as being a sequence of at least 3, preferably 3-5, particularly preferably 5-7, and even very particularly preferably 7-20, amino acids from the a determinant of the novel HBV variant, with mixtures of such polypeptide fragments also being encompassed by this invention.

The present invention also encompasses an isolated nucleotide sequence which can be hybridized and leads to nucleotide sequences which correspond to the nucleotide sequences of the HBsAg of the novel HBV variant or parts of the a determinant of the novel HBV variant, are complementary thereto, or are to be traced back to HDB 05 as a subtype or mutation.

The skilled person is familiar with the fact that, after its isolation using methods in accordance with the prior art, a nucleotide sequence can be introduced into prokaryotic (e.g. *E. coli*) or eukaryotic host cells (e.g. Chinese hamster ovary cell) or yeast (e.g. *S. Cerevisiae*) with the aid of a vector or construct (using methods known to the skilled person such as transfection, transformation or electroporation: Molecular Cloning: A Laboratory Manual, 2nd ed., Vol. 1-3, ed Sambrook et al., Cold Spring Harbor Laboratory Press (1989), with it being possible to use transient or permanent cultures.

Consequently, the present invention encompasses isolated nucleotide sequences of the a determinant of the novel HBV variant, polypeptides which are encoded by these nucleotides, vectors which contain nucleotide sequences of the a determinant of the novel HBV variant, and also the host cell into which a vector is introduced.

In addition to using an expression system to prepare polypeptides (recombinantly), it is obvious that analogous polypeptide structures are also prepared synthetically or directly by purification from the virus variant.

It is possible to use the polypeptides or proteins of the novel HBV variant to generate monoclonal and/or polyclonal antibodies which bind immunologically to binding sites (epitopes) of the a determinant of the novel HBV variant. The methods for preparing antibodies are known to the skilled person (e.g. Koehler et al., Nature 256-495 (1975), Mimms et al., Vi. 176: 604-619 (1990).

It is furthermore possible to use the a determinant of the HDB 05 variant according to the invention, in the form of the entire polypeptide sequence or parts thereof, for determining antibodies which are directed against the HBV variant: anti-HBs antibodies.

The skilled person is familiar with a large number of determination methods in which immune complexes are formed, or their formation is inhibited, using polypeptides from the a determinant of the HBV variant and antibodies of animal or human origin.

Finally, it is possible to use monoclonal or polyclonal antibodies (or mixtures or fragments thereof or mixtures of fragments) which react with epitopes of the novel HBV variant to determine the a determinant of the HBV variant according to the invention in the form of the entire polypeptide sequence, or parts thereof, in samples under investigation: HBsAg of the HDB 05 variant.

The skilled person is familiar with a large number of determination methods in which immune complexes are formed, or their formation is inhibited, using one or more monoclonal antibody(ies) or polyclonal antibodies (or mixtures thereof or fragments or mixtures of fragments) which are specific for the a determinant of the HBV variant.

It is likewise possible to develop corresponding primers on the basis of the nucleotide sequences of the novel HBV variant which have been found.

Finally, the invention also relates to diagnostic reagents as kits which, based on the above-described methods make possible the detection of HBV variant-specific antigen (HBsAg) or antibodies directed against it (anti-HBs), either as single determinations or combined with each other or with other known HBV antigens or antibodies which react specifically therewith or else with quite different analytes.

In addition, the present invention is described in the patent claims.

DESCRIPTION OF THE FIGURES

FIG. 1 presents an overview of the amino acid sequences of the a determinant of 6 described HBV genotypes in comparison with HDB 05.

FIG. 2 depicts the nucleotide and amino acid sequences of the a determinant, as well as immediately adjacent regions of the HBV genotype A, subtype adw.

FIG. 3 shows the nucleotide sequence of the a determinant of the HBV surface antigen for subtype adw of HBV genotype A as compared with the nucleotide sequence of HDB 05.

FIG. 4 summarizes the translation-relevant differences in the nucleotide sequence of HDB 05.

FIG. 5 depicts the nucleotide sequence of HDB 05 in the region of the a determinant, as well as the corresponding amino acid sequence. The a determinant is located between amino acids No. 101 and 180 of the small HBsAg (small, S).

FIG. 6 shows the corresponding polypeptide sequence of the a determinant of HDB 05, which polypeptide sequence is encoded by the nucleotide sequence described in FIG. 5.

The following examples explain the present invention in more detail, without the invention being restricted to the examples which are described.

EXAMPLE 1

Using Enzyme Immunoassay, EIA, to Determine HBsAg

The enzyme immunoassay Enzygnost® HBsAg 5.0 from Dade Behring GmbH, Marburg, Germany, was used to determine the HBV surface antigen, i.e. HBsAg, in the blood of the patients from France and Austria.

It is a high-performance test which is approved in Europe and which was performed in accordance with the instructions in the pack information leaflet.

The underlying test principle is a sandwich test in microtiter plate format:

100 µl of the sample to be investigated are brought into contact, in a one-step method, with 25 µl of conjugate 1 (mouse monoclonal HBsAg-specific antibodies which are covalently labeled with biotin) and immobilized sheep polyclonal HBsAg-specific antibodies. After a 60-minute incubation at 37° C., and after removing excess components by washing the plate wells 4 times, 100 µl of conjugate 2, which consists of streptavidin to which the probe enzyme peroxidase is covalently bonded, are added.

After a 30-minute incubation at 37° C., and after having removed excess components by washing the plate wells 4 times, 75 µl of chromogen buffer/substrate solution are added, with this being followed by a 30-minute incubation at room temperature. The development of the blue tetramethylbenzidine dye is terminated by adding 75 µl of stopping solution (sulfuric acid) and the dye is measured photometrically at 450 nm.

The intensity of the color which develops, as measured by the optical density (O.D.), is directly proportional to the content of HBsAg in the investigated sample, with an O.D. value of less than the threshold value being assessed as HBsAg-negative. The threshold value is defined as the mean value of the O.D of the negative control (contained in the test kit) which is tested in parallel, to which a constant quantity of 0.05 O.D. is added.

The detection limits of the batch (#32874) which was used for the investigation were determined, by means of graphic interpolation and using the internationally accepted standard preparations from the Paul Ehrlich Institute, Langen, Germany, to be 0.012 ng of ad subtype/ml and, respectively, 0.015 ng of ay subtype/ml in parallel with the experimental assays from tests of dilutions of the standard preparations in HBsAg-negative serum.

Analysis of the samples #119617 and 118234 from which the DNA was also isolated, gave results, for both samples of between 0.02 and 0.05 O.D in 2 independent experiments on two different days, which results are to be interpreted, in accordance with the criteria of the test, as being HBsAg-negative. On the other hand, the positive control (contained in the test kit) which was concomitantly assayed was as positive (validation criteria fulfilled) as the abovementioned ad and ay standard preparations.

EXAMPLE 2

Isolating the HDB 05 DNA from sample #118234

The QIA Amp® DNA blood mini kit from Qiagen, Hilden, Germany, was used to isolate the DNA from in each case a 200 µl aliquot of the French and Austrian samples. In doing this, all the procedural steps were followed as described in the pack information leaflet and the elution was performed in a volume of 50 µl in each case.

EXAMPLE 3

Polymerase Chain Reaction, PCR 3.1 HBV Primers

The four HBV primers listed below were used:

```
Primer 1 having the 5'>3' sequence:    (SEQ ID NO: 23)
GGGTCACCATATTCTTGGGAAC Primer 2 having the 5'>3' sequence:    (SEQ ID NO: 24)
TATACCCAAAGACAAAAGAAAATTGG Primer 3 having the 5'>3' sequence:    (SEQ ID NO: 25)
GACTCGTGGTGGACTTCTCTC Primer 4 having the 5'>3' sequence:    (SEQ ID NO: 26)
TACAGACTTGGCCCCCAATACC
```

3.2 PCR Amplification

The Perkin Elmer Ampli Taq® DNA polymerase kit as well as the Thermocycler Gene Amp® PCR system 9700 from Perkin Elmer Applied Biosystems, USA, were used to carry out a nested PCR amplification of the surface antigen.

The nucleotides were obtained from Amersham Biosciences, UK.

For the first amplification cycle, 5 µl of the isolated DNA were amplified using the abovementioned primers 1 and 2 and the following conditions:

| PCR 1 rxn | |
|---|---|
| Primer 1 (10 µM) | 1 µl |
| Primer 2 (10 µM) | 1 µl |
| 10-fold conc. buffer (incl. 15 µM MgCl$_2$) | 5 µl |
| dNTP mixture (10 µm) | 1 µl |
| dist. Water | 36.75 µl |
| Ampli Taq (5 U/µl) | 0.25 µl |
| (per tube) | 45 µl total volume |
| plus | 5 µl of isolated DNA |
| | 50 µl reaction volume |

The 50 µl assay was amplified using the above-described thermocycler under the following conditions:

94° C., 1 min./94° C., 28 sec.—55° C., 28 sec.—72° C., 38 sec. (35 cycles)/72° C., 5 min./8° C. soak.

In the second round of amplification, 5 µl of the first PCR product were further amplified using the HBV primers 3 and 4 and the following conditions:

| PCR 2 rxn | |
|---|---|
| Primer 3 (10 µM) | 1 µl |
| Primer 4 (10 µM) | 1 µl |
| 10-fold conc. buffer | 5 µl |
| dNTP mixture (10 µM) | 1 µl |

-continued

| PCR 2 rxn | |
|---|---|
| dist. Water | 36.75 µl |
| Ampli Taq (5 U/µl) | 0.25 µl |
| per tube | 45 µl total volume |
| plus | 5 µl of PCR product v. rxn |
| | 50 µl reaction_volume |

This PCR 2 assay was amplified using the above-described thermocycler and employing the following conditions: 94° C., 1 min./94° C., 28 sec.—55° C., 28 sec.—72° C., 38 sec. (35 cycles)/72° C., 5 min./8° C. soak.

In conclusion, the PCR 2 product was fractionated electrophoretically (1.5% agarose) while including suitable molecular weight markers. The band containing approx. 520 base pairs was excised and isolated using the QIA quick gel extraction kit from Qiagen, Hilden, Germany.

EXAMPLE 4

Sequencing HDB 05

The purified PCR product was sequenced by Medigenomix, Martinsried, Germany, with the aid of the ABI 3700 Kapillar system in combination with the ABI BigDye Terminator Chemistry Version 1.1. and the ABI Sequencing Analysis Software Version 3.6. and using the primers 3 and 4 described in Ex. 3.

Sequencing Results

It was shown that the HBsAgs of the two analyzed samples agreed with each other and that, within the sequenced region, the nucleotide and amino acid sequences exhibited the best agreement with genotype A, subtype adw. In agreement with each other, the analyzed samples from France and Austria exhibited a total of 4 amino acid substitutions in the region of the a determinant as compared with genotype A, subtype adw (see also FIGS. 2 and 5):

| HDB 05 | | A, adw |
|---|---|---|
| 1.) | Arg (R) | substituted for 115 Thr (T) |
| 2.) | Gln (Q) | substituted for 120 Pro (P) |
| 3.) | Leu (L) | substituted for 154 Ser (S) |
| 4.) | Val (V) | substituted for 164 Glu (E) |
| In addition, there is an amino acid substitution at position # 181: | | |
| 5.) | Arg (R) | substituted for 181 Gln (Q). |

These results were reproduced, with the same sequencing results, in several independent analyses of the two investigated blood samples from France and Austria, with the sequencing results furthermore exhibiting complete agreement in the case of the two independent samples.

The invention claimed is:

1. An isolated or purified oligopeptide or polypeptide comprising an amino acid sequence with at least 94% identity to SEQ ID NO:13 in which:
   (i) from 0 to 4 amino acids are substituted, deleted, or inserted as compared with SEQ ID NO:13, and
   (ii) at least one of the five amino acid substitutions in the S antigen of the hepatitis B variant HDB 05 as compared to the HBV adw wild type is preserved, wherein said substitutions are chosen from T 115 (R), P 120 (Q), S 154 (L), E 164 (V), and Q 181 (R) of the S antigen of HBV.

2. The oligopeptide or polypeptide of claim 1, wherein the oligopeptide or polypeptide reacts with sera from individuals who are infected with the hepatitis B variant HDB 05.

3. An isolated or purified oligopeptide or polypeptide, comprising an amino acid sequence with at least 94% identity to SEQ ID NO:13 in which:

(i) from 0 to 4 amino acids are substituted, deleted or inserted as compared with SEQ ID NO:13, and (ii) at least two of the five amino acid substitutions in the S antigen of the hepatitis B variant HDB 05 as compared to the HBV adw wild type are preserved, wherein said substitutions are chosen from T 115 (R), P 120 (Q), S 154 (L), E 164 (V), and Q 181 (R) of the S antigen of HBV.

4. The oligopeptide or polypeptide of claim 3, wherein the oligopeptide or polypeptide reacts with sera from individuals who are infected with the hepatitis B variant HDB 05.

5. An isolated or purified oligopeptide or polypeptide comprising a fragment of SEQ ID NO:12, wherein the fragment of SEQ ID NO:12 comprises at least one of the following sequences:

(i) a sequence of at least 8 consecutive amino acids that includes amino acid position 73 of SEQ ID NO:12 and is found within positions 66-80 of SEQ ID NO:12;

(ii) a sequence of at least 6 consecutive amino acids that includes amino acid position 78 of SEQ ID NO:12 and is found within positions 73-83 of SEQ ID NO:12;

(iii) a sequence of at least 6 consecutive amino acids that includes amino acid position 112 of SEQ ID NO:12 and is found within positions 107-117 of SEQ ID NO:12;

(iv) a sequence of at least 30 consecutive amino acids that includes amino acid position 122 of SEQ ID NO:12 and is found within positions 93-151 of SEQ ID NO:12; and (v) a sequence of at least 6 consecutive amino acids that includes amino acid position 139 of SEQ ID NO:12 and is found within positions 134-144 of SEQ ID NO:12.

6. The oligopeptide or polypeptide of claim 5, comprising an amino acid sequence chosen from SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22.

7. The oligopeptide or polypeptide of claim 5, wherein the oligopeptide or polypeptide reacts with sera from individuals who are infected with the hepatitis B variant HDB 05.

8. A composition comprising at least one immunogenic molecule comprising one or more oligopeptides or polypeptides as claimed in one of claim 1, 3, 5, or 6, and optionally further comprising one or more HBV immunogens.

9. A method of preparing the oligopeptide or polypeptide as claimed in one of claim 1, 3, 5, or 6, which comprises culturing a cell and expressing the oligopeptide or polypeptide in said cell.

10. The method as claimed in claim 9, wherein the oligopeptide or polypeptide is isolated from the cells and separated from other oligopeptides or polypeptides.

11. A kit for detecting hepatitis B viruses, comprising at least one of (i) an oligopeptide or polypeptide as claimed in one of claim 1, 3, 5, or 6; (ii) an oligonucleotide or polynucleotide encoding said oligopeptide or polypeptide; and (iii) an antibody which recognizes said oligopeptide or polypeptide.

12. A method of identifying antibodies directed against a hepatitis B antigen, comprising (a) incubating a sample with an oligopeptide or polypeptide as claimed in one of claim 1, 3, 5, or 6, under conditions which allow the formation of antigen-antibody complexes; and (b) detecting antibody-antigen complexes comprising said oligopeptide or polypeptide.

13. The isolated or purified oligopeptide or polypeptide of claim 1, wherein at least three of the five amino acid substitutions in the S antigen of the hepatitis B variant HDB 05 as compared to the HBV adw wild type are preserved, wherein said substitutions are chosen from T 115 (R), P 120 (Q), S 154 (L), E 164 (V), and Q 181 (R).

14. The isolated or purified oligopeptide or polypeptide of claim 1, wherein at least four of the five amino acid substitutions in the S antigen of the hepatitis B variant HDB 05 as compared to the HBV adw wild type are preserved, wherein said substitutions are chosen from T 115 (R), P 120 (Q), S 154 (L), E 164 (V), and Q 181 (R).

15. The isolated or purified oligopeptide or polypeptide of claim 1, wherein the five amino acid substitutions in the S antigen of the hepatitis B variant HDB 05 as compared to the HBV adw wild type are preserved, wherein said substitutions are chosen from T 115 (R), P 120 (Q), S 154 (L), E 164 (V), and Q 181 (R).

16. The oligopeptide or polypeptide of claim 2, wherein the region of the amino acid sequence that reacts with the sera is chosen from at least one of the regions corresponding to amino acids 115 to 120, amino acids 154 to 164, and amino acid 154 to 185 of the S antigen of HBV.

17. The isolated or purified oligopeptide or polypeptide of claim 15,
   wherein the oligopeptide or polypeptide reacts with sera from individuals who are infected with the hepatitis B variant HDB 05; and
   wherein the region of the amino acid sequence that reacts with the sera is chosen from at least one of the regions corresponding to amino acids 115 to 120, amino acids 154 to 164, and amino acid 154 to 185 of the S antigen of HBV.

18. The isolated or purified oligopeptide or polypeptide of claim 1,
   wherein at least two of the five amino acid substitutions in the S antigen of the hepatitis B variant HDB 05 as compared to the HBV adw wild type are preserved,
   wherein said substitutions are chosen from T 115 (R), P 120 (Q), S 154 (L), E 164 (V), and Q 181 (R); and
   wherein the oligopeptide or polypeptide reacts with sera from individuals who are infected with the hepatitis B variant HDB 05; and
   wherein the region of the amino acid sequence that reacts with the sera is chosen from at least one of the regions corresponding to amino acids 115 to 120, amino acids 154 to 164, and amino acid 154 to 185 of the S antigen of HBV.

19. The isolated or purified oligopeptide or polypeptide of claim 5,
   wherein the oligopeptide or polypeptide reacts with sera from individuals who are infected with the hepatitis B variant HDB 05; and
   wherein the region of the amino acid sequence that reacts with the sera is chosen from at least one of the regions corresponding to amino acids 115 to 120, amino acids 154 to 164, and amino acid 154 to 185 of the S antigen of HBV.

20. An isolated or purified oligopeptide or polypeptide comprising a fragment of SEQ ID NO:12, wherein the fragment of SEQ ID NO:12 comprises at least two of the following sequences:
   (i) a sequence of at least 5 consecutive amino acids that includes amino acid position 73 of SEQ ID NO:12 and is found within positions 69-77 of SEQ ID NO:12;
   (ii) a sequence of at least 5 consecutive amino acids that includes amino acid position 78 of SEQ ID NO:12 and is found within positions 74-82 of SEQ ID NO:12;
   (iii) a sequence of at least 5 consecutive amino acids that includes amino acid position 112 of SEQ ID NO:12 and is found within positions 108-116 of SEQ ID NO:12;
   (iv) a sequence of at least 5 consecutive amino acids that includes amino acid position 122 of SEQ ID NO:12 and is found within positions 118-126 of SEQ ID NO:12; and
   (v) a sequence of at least 5 consecutive amino acids that includes amino acid position 139 of SEQ ID NO:12 and is found within positions 135-143 of SEQ ID NO:12.

21. An isolated or purified oligopeptide or polypeptide comprising a fragment of SEQ ID NO:12, wherein the fragment of SEQ ID NO:12 comprises at least three of the following sequences:
   (i) a sequence of at least 5 consecutive amino acids that includes amino acid position 73 of SEQ ID NO:12 and is found within positions 69-77 of SEQ ID NO:12;
   (ii) a sequence of at least 5 consecutive amino acids that includes amino acid position 78 of SEQ ID NO:12 and is found within positions 74-82 of SEQ ID NO:12;
   (iii) a sequence of at least 5 consecutive amino acids that includes amino acid position 112 of SEQ ID NO:12 and is found within positions 108-116 of SEQ ID NO:12;
   (iv) a sequence of at least 5 consecutive amino acids that includes amino acid position 122 of SEQ ID NO:12 and is found within positions 118-126 of SEQ ID NO:12; and
   (v) a sequence of at least 5 consecutive amino acids that includes amino acid position 139 of SEQ ID NO:12 and is found within positions 135-143 of SEQ ID NO:12.

22. An isolated or purified oligopeptide or polypeptide comprising a fragment of SEQ ID NO:12, wherein the fragment of SEQ ID NO:12 comprises at least four of the following sequences:
   (i) a sequence of at least 5 consecutive amino acids that includes amino acid position 73 of SEQ ID NO:12 and is found within positions 69-77 of SEQ ID NO:12;
   (ii) a sequence of at least 5 consecutive amino acids that includes amino acid position 78 of SEQ ID NO:12 and is found within positions 74-82 of SEQ ID NO:12;
   (iii) a sequence of at least 5 consecutive amino acids that includes amino acid position 112 of SEQ ID NO:12 and is found within positions 108-116 of SEQ ID NO:12;
   (iv) a sequence of at least 5 consecutive amino acids that includes amino acid position 122 of SEQ ID NO:12 and is found within positions 118-126 of SEQ ID NO:12; and
   (v) a sequence of at least 5 consecutive amino acids that includes amino acid position 139 of SEQ ID NO:12 and is found within positions 135-143 of SEQ ID NO:12.

23. An isolated or purified oligopeptide or polypeptide comprising a fragment of SEQ ID NO:12, wherein the fragment of SEQ ID NO:12 comprises:
   (i) a sequence of at least 5 consecutive amino acids that includes amino acid position 73 of SEQ ID NO:12 and is found within positions 69-77 of SEQ ID NO:12;
   (ii) a sequence of at least 5 consecutive amino acids that includes amino acid position 78 of SEQ ID NO:12 and is found within positions 74-82 of SEQ ID NO:12;
   (iii) a sequence of at least 5 consecutive amino acids that includes amino acid position 112 of SEQ ID NO:12 and is found within positions 108-116 of SEQ ID NO:12;
   (iv) a sequence of at least 5 consecutive amino acids that includes amino acid position 122 of SEQ ID NO:12 and is found within positions 118-126 of SEQ ID NO:12; and
   (v) a sequence of at least 5 consecutive amino acids that includes amino acid position 139 of SEQ ID NO:12 and is found within positions 135-143 of SEQ ID NO:12.

\* \* \* \* \*

SEQUENCE LISTING

```
<160> NUMBER OF SEQ ID NOS: 26

<210> SEQ ID NO 1
<211> LENGTH: 462
<212> TYPE: DNA
<213> ORGANISM: Hepatitis B virus

<400> SEQUENCE: 1
gggggatcac ccgtgtgtct tggccaaaat tcgcagtccc caacctccaa tcactcacca      60
acctcctgtc ctccaatttg tcctggttat cgctggatgt gtctgcggcg ttttatcata     120
ttcctcttca tcctgctgct atgcctcatc ttcttattgg ttcttctgga ttatcaaggt     180
atgttgcccg tttgtcctct aattccagga tcaacaagaa ccagtacggg acaatgcaaa     240
acctgcacga ctcctgctca aggcaactct atgtttccct catgttgctg tacaaaacct     300
acggatggaa attgcacctg tattcccatc ccattgtcct gggctttcgc aaaataccta     360
tgggtgtggg cctcagtccg tttctcttgg ctcagtttac tagtgccatt tgttcggtgg     420
ttcgtagggc tttcccccac tgtttggctt tcagctatat gg                        462

<210> SEQ ID NO 2
<211> LENGTH: 225
<212> TYPE: DNA
<213> ORGANISM: Hepatitis B virus

<400> SEQUENCE: 2
ccaggatcaa caagaaccag tacgggacaa tgcaaaacct gcacgactcc tgctcaaggc      60
aactctatgt ttccctcatg ttgctgtaca aaacctacgg atggaaattg cacctgtatt     120
cccatcccat tgtcctgggc tttcgcaaaa tacctatggg tgtgggcctc agtccgtttc     180
tcttggctca gtttactagt gccatttgtt cggtggttcg taggg                     225
```

```
<210> SEQ ID NO 3
<211> LENGTH: 180
<212> TYPE: DNA
<213> ORGANISM: Hepatitis B virus

<400> SEQUENCE: 3
ccaggatcaa caagaaccag tacgggacaa tgcaaaacct gcacgactcc tgctcaaggc      60
aactctatgt ttccctcatg ttgctgtaca aaacctacgg atggaaattg cacctgtatt     120
cccatcccat tgtcctgggc tttcgcaaaa tacctatggg tgtgggcctc agtccgtttc     180

<210> SEQ ID NO 4
<211> LENGTH: 165
<212> TYPE: DNA
<213> ORGANISM: Hepatitis B virus

<400> SEQUENCE: 4
ccaggatcaa caagaaccag tacgggacaa tgcaaaacct gcacgactcc tgctcaaggc      60
aactctatgt ttccctcatg ttgctgtaca aaacctacgg atggaaattg cacctgtatt     120
cccatcccat tgtcctgggc tttcgcaaaa tacctatggg tgtgg                     165

<210> SEQ ID NO 5
<211> LENGTH: 60
<212> TYPE: DNA
<213> ORGANISM: Hepatitis B virus

<400> SEQUENCE: 5
ccaggatcaa caagaaccag tacgggacaa tgcaaaacct gcacgactcc tgctcaaggc      60

<210> SEQ ID NO 6
<211> LENGTH: 30
<212> TYPE: DNA
<213> ORGANISM: Hepatitis B virus

<400> SEQUENCE: 6
ccaggatcaa caagaaccag tacgggacaa                                       30

<210> SEQ ID NO 7
<211> LENGTH: 153
<212> TYPE: DNA
<213> ORGANISM: Hepatitis B virus

<400> SEQUENCE: 7
agaaccagta cgggacaatg caaaacctgc acgactcctg ctcaaggcaa ctctatgttt      60
ccctcatgtt gctgtacaaa acctacggat ggaaattgca cctgtattcc catcccattg     120
tcctgggctt tcgcaaaata cctatgggtg tgg                                  153

<210> SEQ ID NO 8
<211> LENGTH: 18
<212> TYPE: DNA
<213> ORGANISM: Hepatitis B virus

<400> SEQUENCE: 8
agaaccagta cgggacaa                                                    18

<210> SEQ ID NO 9
<211> LENGTH: 96
<212> TYPE: DNA
<213> ORGANISM: Hepatitis B virus

<400> SEQUENCE: 9
ttgtcctggg ctttcgcaaa atacctatgg gtgtgggcct cagtccgttt ctcttggctc      60
```

```
agtttactag tgccatttgt tcggtggttc gtaggg                              96
```

\<210\> SEQ ID NO 10
\<211\> LENGTH: 51
\<212\> TYPE: DNA
\<213\> ORGANISM: Hepatitis B virus

\<400\> SEQUENCE: 10

```
ttgtcctggg ctttcgcaaa atacctatgg gtgtgggcct cagtccgttt c            51
```

\<210\> SEQ ID NO 11
\<211\> LENGTH: 36
\<212\> TYPE: DNA
\<213\> ORGANISM: Hepatitis B virus

\<400\> SEQUENCE: 11

```
ttgtcctggg ctttcgcaaa atacctatgg gtgtgg                             36
```

\<210\> SEQ ID NO 12
\<211\> LENGTH: 154
\<212\> TYPE: PRT
\<213\> ORGANISM: Hepatitis B virus

\<400\> SEQUENCE: 12

```
Gly Gly Ser Pro Val Cys Leu Gly Gln Asn Ser Gln Ser Pro Thr Ser
1               5                   10                  15
Asn His Ser Pro Thr Ser Cys Pro Pro Ile Cys Pro Gly Tyr Arg Trp
            20                  25                  30
Met Cys Leu Arg Arg Phe Ile Ile Phe Leu Phe Ile Leu Leu Leu Cys
        35                  40                  45
Leu Ile Phe Leu Leu Val Leu Leu Asp Tyr Gln Gly Met Leu Pro Val
    50                  55                  60
Cys Pro Leu Ile Pro Gly Ser Thr Arg Thr Ser Thr Gly Gln Cys Lys
65                  70                  75                  80
Thr Cys Thr Thr Pro Ala Gln Gly Asn Ser Met Phe Pro Ser Cys Cys
                85                  90                  95
Cys Thr Lys Pro Thr Asp Gly Asn Cys Thr Cys Ile Pro Ile Pro Leu
            100                 105                 110
Ser Trp Ala Phe Ala Lys Tyr Leu Trp Val Trp Ala Ser Val Arg Phe
        115                 120                 125
Ser Trp Leu Ser Leu Leu Val Pro Phe Val Arg Trp Phe Val Gly Leu
    130                 135                 140
Ser Pro Thr Val Trp Leu Ser Ala Ile Trp
145                 150
```

\<210\> SEQ ID NO 13
\<211\> LENGTH: 75
\<212\> TYPE: PRT
\<213\> ORGANISM: Hepatitis B virus

\<400\> SEQUENCE: 13

```
Pro Gly Ser Thr Arg Thr Ser Thr Gly Gln Cys Lys Thr Cys Thr
1               5                   10                  15
Pro Ala Gln Gly Asn Ser Met Phe Pro Ser Cys Cys Thr Lys Pro
            20                  25                  30
Thr Asp Gly Asn Cys Thr Cys Ile Pro Ile Pro Leu Ser Trp Ala Phe
        35                  40                  45
Ala Lys Tyr Leu Trp Val Trp Ala Ser Val Arg Phe Ser Trp Leu Ser
    50                  55                  60
```

```
Leu Leu Val Pro Phe Val Arg Trp Phe Val Gly
 65                  70                  75
```

<210> SEQ ID NO 14
<211> LENGTH: 60
<212> TYPE: PRT
<213> ORGANISM: Hepatitis B virus

<400> SEQUENCE: 14

```
Pro Gly Ser Thr Arg Thr Ser Thr Gly Gln Cys Lys Thr Cys Thr Thr
  1               5                  10                  15

Pro Ala Gln Gly Asn Ser Met Phe Pro Ser Cys Cys Cys Thr Lys Pro
             20                  25                  30

Thr Asp Gly Asn Cys Thr Cys Ile Pro Ile Pro Leu Ser Trp Ala Phe
         35                  40                  45

Ala Lys Tyr Leu Trp Val Trp Ala Ser Val Arg Phe
     50                  55                  60
```

<210> SEQ ID NO 15
<211> LENGTH: 55
<212> TYPE: PRT
<213> ORGANISM: Hepatitis B virus

<400> SEQUENCE: 15

```
Pro Gly Ser Thr Arg Thr Ser Thr Gly Gln Cys Lys Thr Cys Thr Thr
  1               5                  10                  15

Pro Ala Gln Gly Asn Ser Met Phe Pro Ser Cys Cys Cys Thr Lys Pro
             20                  25                  30

Thr Asp Gly Asn Cys Thr Cys Ile Pro Ile Pro Leu Ser Trp Ala Phe
         35                  40                  45

Ala Lys Tyr Leu Trp Val Trp
     50                  55
```

<210> SEQ ID NO 16
<211> LENGTH: 20
<212> TYPE: PRT
<213> ORGANISM: Hepatitis B virus

<400> SEQUENCE: 16

```
Pro Gly Ser Thr Arg Thr Ser Thr Gly Gln Cys Lys Thr Cys Thr Thr
  1               5                  10                  15

Pro Ala Gln Gly
             20
```

<210> SEQ ID NO 17
<211> LENGTH: 10
<212> TYPE: PRT
<213> ORGANISM: Hepatitis B virus

<400> SEQUENCE: 17

```
Pro Gly Ser Thr Arg Thr Ser Thr Gly Gln
  1               5                  10
```

<210> SEQ ID NO 18
<211> LENGTH: 51
<212> TYPE: PRT
<213> ORGANISM: Hepatitis B virus

<400> SEQUENCE: 18

```
Arg Thr Ser Thr Gly Gln Cys Lys Thr Cys Thr Thr Pro Ala Gln Gly
  1               5                  10                  15
```

Asn Ser Met Phe Pro Ser Cys Cys Thr Lys Pro Thr Asp Gly Asn
            20                  25                  30

Cys Thr Cys Ile Pro Ile Pro Leu Ser Trp Ala Phe Ala Lys Tyr Leu
        35                  40                  45

Trp Val Trp
    50

<210> SEQ ID NO 19
<211> LENGTH: 6
<212> TYPE: PRT
<213> ORGANISM: Hepatitis B virus

<400> SEQUENCE: 19

Arg Thr Ser Thr Gly Gln
1               5

<210> SEQ ID NO 20
<211> LENGTH: 36
<212> TYPE: PRT
<213> ORGANISM: Hepatitis B virus

<400> SEQUENCE: 20

Pro Ile Pro Leu Ser Trp Ala Phe Ala Lys Tyr Leu Trp Val Trp Ala
1               5                   10                  15

Ser Val Arg Phe Ser Trp Leu Ser Leu Leu Val Pro Phe Val Arg Trp
            20                  25                  30

Phe Val Gly Leu
        35

<210> SEQ ID NO 21
<211> LENGTH: 20
<212> TYPE: PRT
<213> ORGANISM: Hepatitis B virus

<400> SEQUENCE: 21

Pro Ile Pro Leu Ser Trp Ala Phe Ala Lys Tyr Leu Trp Val Trp Ala
1               5                   10                  15

Ser Val Arg Phe
            20

<210> SEQ ID NO 22
<211> LENGTH: 15
<212> TYPE: PRT
<213> ORGANISM: Hepatitis B virus

<400> SEQUENCE: 22

Pro Ile Pro Leu Ser Trp Ala Phe Ala Lys Tyr Leu Trp Val Trp
1               5                   10                  15

<210> SEQ ID NO 23
<211> LENGTH: 22
<212> TYPE: DNA
<213> ORGANISM: Artificial Sequence
<220> FEATURE:
<223> OTHER INFORMATION: Primer 1

<400> SEQUENCE: 23
gggtcaccat attcttggga ac                                            22

<210> SEQ ID NO 24
<211> LENGTH: 26
<212> TYPE: DNA
<213> ORGANISM: Artificial Sequence
<220> FEATURE:

```
<223> OTHER INFORMATION: Primer 2

<400> SEQUENCE: 24
tatacccaaa gacaaaagaa aattgg                                          26

<210> SEQ ID NO 25
<211> LENGTH: 21
<212> TYPE: DNA
<213> ORGANISM: Artificial Sequence
<220> FEATURE:
<223> OTHER INFORMATION: Primer 3

<400> SEQUENCE: 25
gactcgtggt ggacttctct c                                               21

<210> SEQ ID NO 26
<211> LENGTH: 22
<212> TYPE: DNA
<213> ORGANISM: Artificial Sequence
<220> FEATURE:
<223> OTHER INFORMATION: Primer 4

<400> SEQUENCE: 26
tacagacttg gcccccaata cc                                              22
```